(12) United States Patent
Swartz et al.

(10) Patent No.: US 9,255,901 B2
(45) Date of Patent: Feb. 9, 2016

(54) SYSTEM AND METHOD FOR POST-EXPOSURE DOSIMETRY USING ELECTRON PARAMAGNETIC RESONANCE SPECTROSCOPY

(75) Inventors: Harold M. Swartz, Lyme, NH (US); Jiang Gui, Hanover, NH (US); Xiaoming He, Hanover, NH (US); Piotr Leniewski, W. Lebanon, NH (US); Roberto J. Nicolalde Flores, West Lebanon, NH (US); Benjamin B. Williams, Thetford Center, VT (US); Dean E. Wilcox, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 1135 days.

(21) Appl. No.: 13/061,423

(22) PCT Filed: Aug. 28, 2009

(86) PCT No.: PCT/US2009/055414
§ 371 (c)(1),
(2), (4) Date: Oct. 20, 2011

(87) PCT Pub. No.: WO2010/047879
PCT Pub. Date: Apr. 29, 2010

(65) Prior Publication Data
US 2012/0040304 A1      Feb. 16, 2012

Related U.S. Application Data

(60) Provisional application No. 61/093,338, filed on Aug. 31, 2008.

(51) Int. Cl.
*A61B 1/24* (2006.01)
*G01R 33/30* (2006.01)
(Continued)

(52) U.S. Cl.
CPC ............ *G01N 24/10* (2013.01); *G01R 33/60* (2013.01)

(58) Field of Classification Search
CPC .. G01R 33/60; G01R 33/34084; G01N 24/10; G01T 1/02
USPC .................................................. 324/300–322
See application file for complete search history.

(56) References Cited

U.S. PATENT DOCUMENTS 4,674,513 A * 6/1987 Jasper, Jr. ..................... 600/430
4,994,745 A * 2/1991 Mizuta ......................... 324/316
(Continued)

OTHER PUBLICATIONS

Reyes, R. A., A. Romanyukha, F. Trompier, C. A. Mitchell, I. Clairand, T. De, L. A. Benevides, and H. M. Swartz. "Electron paramagnetic resonance in human fingernails: the sponge model implication." Radiation and environmental biophysics 47, No. 4 (2008): 515-526.*

(Continued)

*Primary Examiner* — Melissa Koval
*Assistant Examiner* — Rishi Patel
(74) *Attorney, Agent, or Firm* — Lathrop & Gage LLP

(57) ABSTRACT

An apparatus and method for triaging patients according to radiation exposure measures electron paramagnetic resonance spectra of fingernails, toenails, and/or teeth. In vivo, radiation induced spectra are obtained from intact fingernails, toenails, or teeth placed within a magnet and with pickup coils over nails between the cut edge at the end of the fingernail and proximal skin or placed adjacent to at least one tooth. The system may also operate in vitro with fingernail clippings. At least three spectra are obtained with one after a delay at above twenty degrees Celsius, and at least one at power levels different from the others. The spectra are used to determine and remove a mechanically induced signal from EPR spectra to determine radiation-induced spectra. The radiation induced spectra are used to determine radiation dose, the dose is compared to triage limits, and a radiological triage tag is printed for the patients.

21 Claims, 14 Drawing Sheets

(51) Int. Cl.
*A61B 10/00* (2006.01)
*A61B 5/055* (2006.01)
*A61B 6/00* (2006.01)
*G01N 24/10* (2006.01)
*G01R 33/60* (2006.01)

(56) References Cited

U.S. PATENT DOCUMENTS

| | | | | |
|---|---|---|---|---|
| 5,030,914 | A | * | 7/1991 | Jasper, Jr. .................. 324/316 |
| 5,725,839 | A | | 3/1998 | Hsia |
| 2004/0251899 | A1 | * | 12/2004 | Swartz et al. .................. 324/316 |
| 2005/0057251 | A1 | * | 3/2005 | Suits et al. .................. 324/318 |
| 2005/0288573 | A1 | | 12/2005 | Timmins |
| 2008/0021256 | A1 | * | 1/2008 | Srinivas et al. .................. 600/3 |
| 2011/0130647 | A1 | * | 6/2011 | Swartz et al. .................. 600/421 |

OTHER PUBLICATIONS

Trompier, F., L. Kornak, C. Calas, A. Romanyukha, B. LeBlanc, C. A. Mitchell, H. M. Swartz, and I. Clairand. "Protocol for emergency EPR dosimetry in fingernails." Radiation measurements 42, No. 6 (2007): 1085-1088.*

Reyes, R. A., et al. "Electron paramagnetic resonance in human fingernails: the sponge model implication." Radiation and environmental biophysics 47.4 (2008): 515-526.*

Romanyukha, A., et al. "EPR dosimetry in chemically treated fingernails." Radiation measurements 42.6 (2007): 1110-1113.*

International Search Report issued in related PCT Patent Application PCT/US2009/055414, dated Apr. 14, 2010, 11 pages.

International Preliminary Report of Patentability issued in related PCT Patent Application PCT/US2009/055414, dated Mar. 20, 2011, 6 pages.

* cited by examiner

SYSTEM AND METHOD FOR POST-EXPOSURE DOSIMETRY USING ELECTRON PARAMAGNETIC RESONANCE SPECTROSCOPY

RELATED APPLICATIONS

The present application claims priority to U.S. Provisional Patent application No. 61/093,338 filed 31 Aug. 2008, which is incorporated herein by reference.

GOVERNMENT RIGHTS

This work was done with U.S. Government funding through National Institutes of Health grant number U19AI067733. This research was also funded through Defense Advanced Research Projects Agency grant numbers HR0011-08-C-0022. In consequence thereof; the United States Government has certain rights in the herein disclosed inventions.

FIELD

The present document relates to the field of electron paramagnetic resonance (also known as electron spin resonance) spectroscopy as applied to measuring radiation doses received by a subject.

BACKGROUND

While most molecules have paired electrons in consequence of covalent bonding, some molecules—including free radicals—have electrons that are not paired. Paired electrons have opposite spins ($M_s=+/-\frac{1}{2}$) that cancel out net magnetic moments. Unpaired electrons have spins that can interact with magnetic fields.

Unpaired electrons in molecules will resonate in a magnetic field. Electron Paramagnetic Resonance Spectroscopy (EPR), sometimes known as Electron Spin Resonance Spectroscopy, takes advantage of this effect to quantify and determine environments of the unpaired electrons. This is done by applying a magnetic field to a substance, which may be located within a human or animal subject, to align spins of any unpaired electrons in the substance. Once spins are aligned, a response of the spins of the unpaired electrons in the substance to radio-frequency electromagnetic radiation at and near a resonant frequency is measured. The resonant frequency and amount of absorption of the electromagnetic radiation is often dependent on the local environment of the unpaired electrons in the molecule as well as the applied magnetic field. The resonance results in such effects as a spike in a radio-frequency absorption spectrum of the substance in a magnetic field.

An EPR spectrum is often acquired by placing a sample in a magnetic field, holding a frequency of a radio frequency source and absorption measuring device constant, and making repeated measurements of response of the sample to the radio frequency energy while sweeping the intensity of the magnetic field. It may also be obtained by repeated measurements made while holding the magnetic field intensity constant and sweeping the frequency of the radio frequency source and measuring device.

Unpaired electrons are naturally found in small quantities in chemicals, such as free radicals, that are found in biological materials. For example, free radicals are produced during, and have importance in oxidative energy production by mitochondria.

It is known that the hydroxyapatite in tooth enamel and keratin in structures, such as fingernails, develop and retain unpaired electrons capable of producing an EPR signal when teeth and fingernails are subjected to ionizing radiation.

In the case of teeth, this EPR signal is roughly proportional to the mass of tooth enamel and to the total radiation dose received in that mass since the tooth formed. This radiation-induced signal has a long half-life.

In the case of fingernails, there is also a radiation induced EPR signal (RIS) having a moderate half-life of at least a few weeks. The RIS is of an intensity that is a function of radiation dose over a range that extends from radiation doses likely to be survived by a subject without treatment, through radiation doses that require medical treatment of a subject for survival, to radiation doses that are fatal to the vast majority of subjects. Ionizing radiation that can create an RIS includes x-ray and gamma-ray radiation such as that emitted by an operating nuclear reactor or a nuclear weapon detonation, as well as radiation emitted by fission products produced by nuclear weapons and reactors.

If the fingernails are clipped, there is also a mechanically-induced EPR signal (MIS) caused by molecular bonds broken when the fingernail is subjected the mechanical stresses of clipping. The MIS is believed to be due at least in part to shearing of Sulfur-Sulfur bonds between cysteine residues of the keratin in the fingernail. Breaking of these bonds leaves a radical that becomes stabilized. This signal is caused in part by the bending fingernail clippings undergo while their edges are being cut, as well as the shearing of cut keratin at the edges of the clipping.

While some decay is seen in the MIS signal, the MIS has a residual component that occurs at similar frequency and magnetic field strength as, and shows some similar characteristics in spectral shape to, any RIS that may be present.

While nuclear reactor operators typically carry dosimeters for measuring radiation that they may be exposed to in a work environment, members of the public, emergency services organizations, and armed forces rarely carry such dosimeters. In the event of nuclear accident, terrorism, or warfare, it would be desirable to measure recent radiation exposure of people exposed to such events. It is proposed that measurement of EPR of fingernails and teeth may provide dosimetry in such people.

Past attempts of dosimetry using EPR of fingernail clippings have found confusion between the RISs and the MIS to be an issue. Not only are components of the MIS found at the same frequency-magnetic field combination as the RIS, but the MIS is of intensity sufficient to obscure the RIS for much of the dose range of interest for triage for acute effects of ionizing radiation. If EPR of fingernail clippings is to be a practical method of dosimetry, it is desirable to find improved ways of reducing interference from the MIS, or of better extracting the RIS component from an overall EPR signal.

Past efforts to reduce the MIS have included soaking the fingernail clippings in water or sodium thioglycolate solutions, these treatments have been found to significantly reduce MIS by allowing radicals at the edges of cut nails to react. The literature and our experiments suggest, however, that the RIS may also affected by soaking and our experiments with water-soaking have not given reproducible and accurate dosimetry results.

Past techniques for measuring EPR signal in teeth have required extraction of a tooth, a procedure unpopular with victims of nuclear disasters.

In an international climate where perpetual enemies, India and Pakistan, are both nuclear powers, where North Korea has nuclear weapons and Iran—a country that has threatened Israel, a country widely believed to be a nuclear power—may soon acquire them, the risk of a nuclear attack or terrorism is increasingly significant. Further, with recent high oil prices and a worldwide resurgence of nuclear power to produce electricity without emitting greenhouse gasses, there is a significant risk of nuclear accident. Nuclear accidents have also resulted from improper disposal of radioactive materials, such as radiation treatment machines.

In nuclear attack, nuclear improper-disposal events, and nuclear accident, there may be people potentially exposed to ionizing radiation while not carrying previously-issued dosimeters. Both nuclear attack and nuclear accident could be mass-casualty situations with several hundred to tens of thousands of people potentially exposed to radiation.

The Chernobyl, Goiânia, Hiroshima, and Nagasaki events each involved at least some deaths from acute radiation syndrome, as have other events. These events also generated demands for measurements of radiation exposure in many thousands of individuals of widely varying radiation exposure, resulting in a substantial stress on the medical systems.

In mass casualty situations there is often mass hysteria, where large numbers of 'worried-well' people physically unaffected by the event may believe that their lives are in danger and may even exhibit psychosomatic symptoms of exposure. This phenomenon is expected to occur in nuclear events such as nuclear attack, terrorism, or accident. Further, there are likely to be limited medical facilities available after some such events—treatment of everyone, the 'worried well' as well as the exposed, is not expected to be possible immediately after a major event.

It is desirable to be able to rapidly sort large numbers of people into categories which may include: those who are 'worried well;' those with minimal exposure-possibly sufficient to cause increased cancer rates or otherwise need follow up—but who will not need treatment for acute radiation sickness; those who have received significant exposure but should recover from acute radiation sickness with conventional therapy; those who should recover from acute radiation sickness with aggressive therapy such as marrow transplants; and those who will probably die regardless of treatment. In the short term, treatment can then be focused upon those groups who most likely will benefit from the treatment. The process of sorting people according to radiation dose or other injuries into treatable, urgently treatable, or untreatable groups is known as triage, and was formalized for non-radiological injuries by the French army as a way to handle the large number of casualties generated on World War I battlefields. Further, if radiation dose can be approximately quantified, this information can be used to help guide patient transport and treatment by determining which people will likely survive with simple supportive care, which will need advanced care such as transfusions, and which will need more drastic measures such as bone-marrow transplant to survive.

In the event of nuclear attack, communications are likely to be disrupted over a large area. In particular, centralized databases, remote locations, the internet, and the cell and landline telephone networks are likely to be nonfunctional or unreachable.

Existing technologies for determining which people of a population have been exposed to large doses of radiation include a differential blood count; neutrophils decrease in number because of bone marrow suppression and lack of replacement, while lymphocytes may undergo apoptosis. Unfortunately, not only do such counts require repeated measurements made by skilled medical staff, but baseline counts are unlikely to be available for the majority of people needing screening and both neutrophil and lymphocyte counts may undergo drastic changes from other causes ranging from HIV infection and stress to infection. A better method of triaging the potentially radiation exposed is needed.

SUMMARY

A device for positioning resonators during EPR of fingernails in vivo has sensor loops in a partial glove for holding the resonators adjacent to fingertips. An alternative device for positioning sensor loops during EPR of fingernails has elastomeric cups for several fingertips that position resonators on the dorsal surface of the fingers adjacent to the fingernails. An alternative device for positioning resonators during EPR of fingernails has hollows for the fingers with coils placed adjacent to the dorsal surface of the fingertips. All three devices combine with a permanent magnet for providing the magnetic field required for resonance, radio frequency apparatus, and a signal processing system to measure a radiation induced EPR signal from fingernails.

A device for EPR of fingernail and/or toenail clippings has a magazine for containing several clipping-holders. The magazine is adapted for passing clipping holders between poles of a magnet with sensor loops for measuring EPR spectra of the fingernails. Radio frequency apparatus and a signal processing system are provided to determine radiation induced EPR signals (RIS) from fingernail clippings in the clipping holders by measuring overall EPR signals and quantifying and subtracting mechanically induced EPR signals (MIS).

A method of triaging subjects involves clipping samples nail from a finger or toe of a subject and measuring EPR spectra of the sample in a magnetic field of at two power levels and after a delay between two of the spectra to estimate components of an MIS from the EPR spectra, and subtracting the MIS from at least one of the spectra to determine an RIS. A wholebody radiation dose of the subject is then estimated from the RIS; and the whole body radiation dose is compared against triage limits.

A device for EPR of teeth in vivo has sensor loops in a plastic chip that can be held between the teeth. The devices for EPR of teeth and fingernails are used to determine EPR spectra that provide a measure of radiation exposure of a subject, a measure which may be of use in triage following a release of radioactive materials or a nuclear attack.

DETAILED DESCRIPTION OF THE EMBODIMENTS

Figure 1:
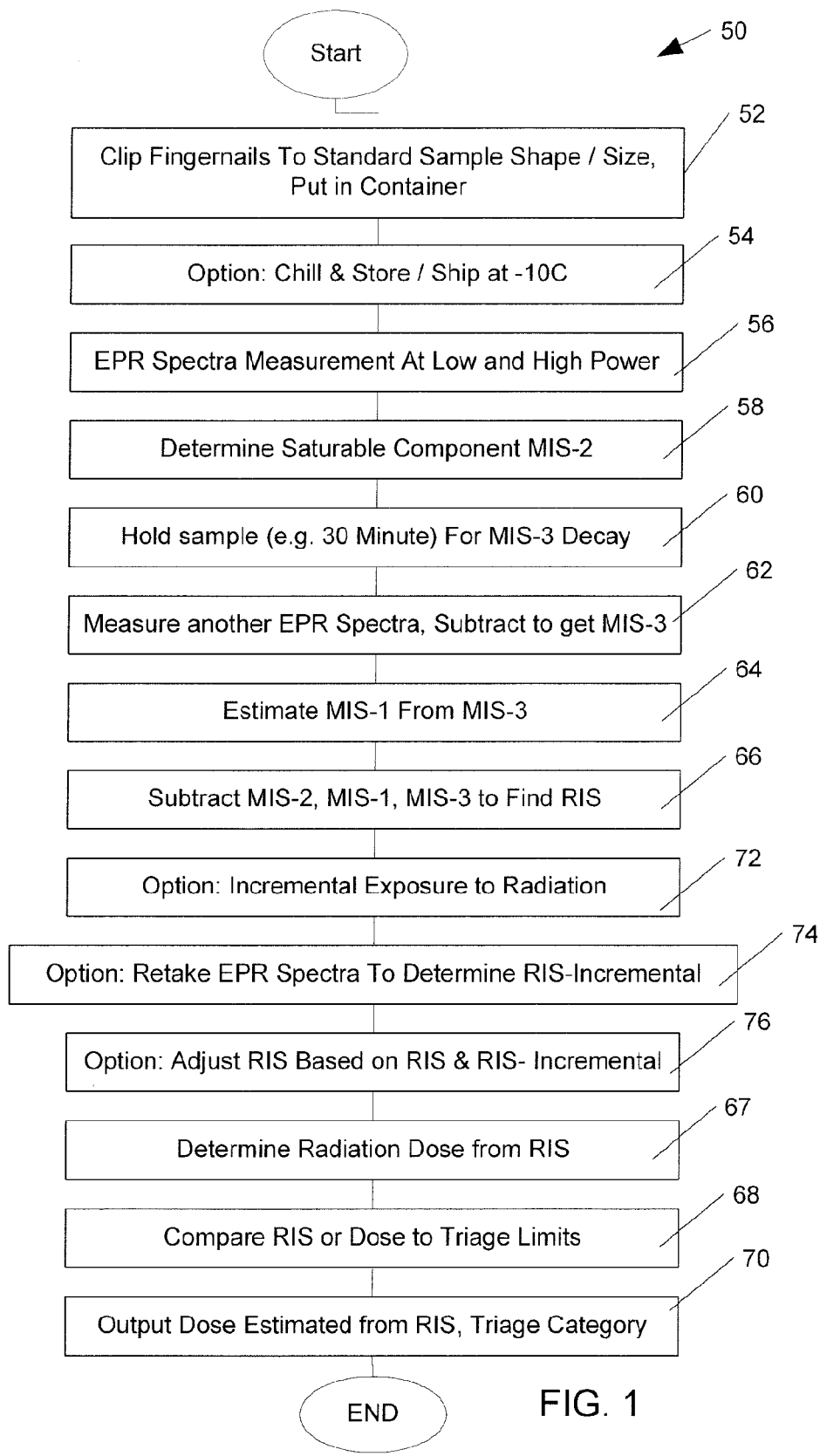
FIG. 1 is a flowchart of an in-vitro method for dosimetry by determining a radiation induced EPR signal (RIS) in fingernail clippings.

An in-vitro method 50 of determining radiation dose experienced by a subject is illustrated in FIG. 1. The method 50 begins with clipping 52 a sample of standardized size and shape of fingernail from a finger of the subject and placing this sample in a standard container. The sample may be immediately chilled 54 to below zero Celsius, and preferably at or below minus ten Celsius, at which temperature it may be stored for several days and may be shipped to a testing machine at a different location than that of the subject. Alternatively, the sample may be subjected to EPR testing immediately without chilling.

The sample is then fed into a testing machine. Within the testing machine, the sample is measured 56 by EPR resonance spectrometry in a magnetic field of at least two thousand gauss, and preferably about three thousand three hundred gauss—a field strength where resonance should occur at about nine to 9.5 gigahertz. The resonance is determined in an embodiment by sweeping frequency of a radio frequency source and observing absorption of radio frequency energy by, and ringing at the end of pulses of radio frequency energy caused by, presence of the sample. In an alternative embodiment, the resonance is determined by sweeping the magnetic field while providing repeated pulses of radio frequency energy and observing absorption of radio frequency energy by, and ringing at the end of pulses of radio frequency energy caused by, presence of the sample.

Figure 2:
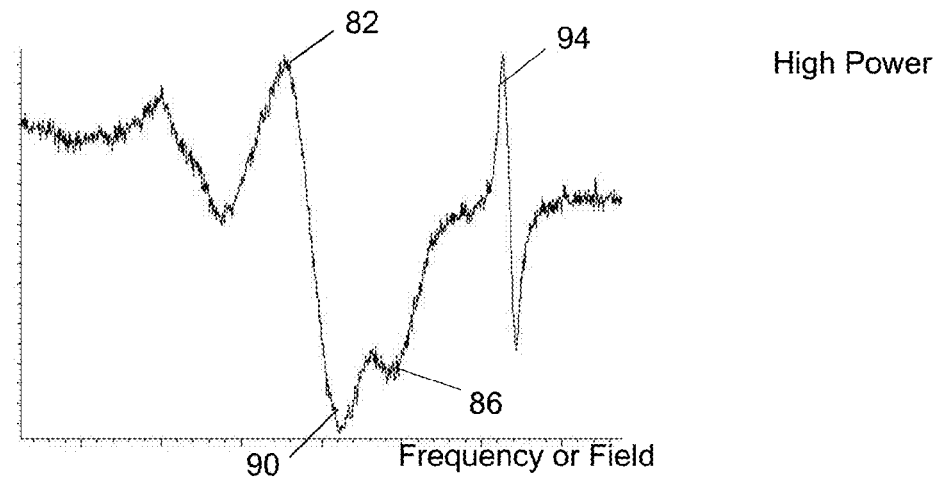
FIG. 2 illustrates resonance intensity versus frequency for a mechanically induced signal in a fingernail sample at high microwave power.
Figure 3:
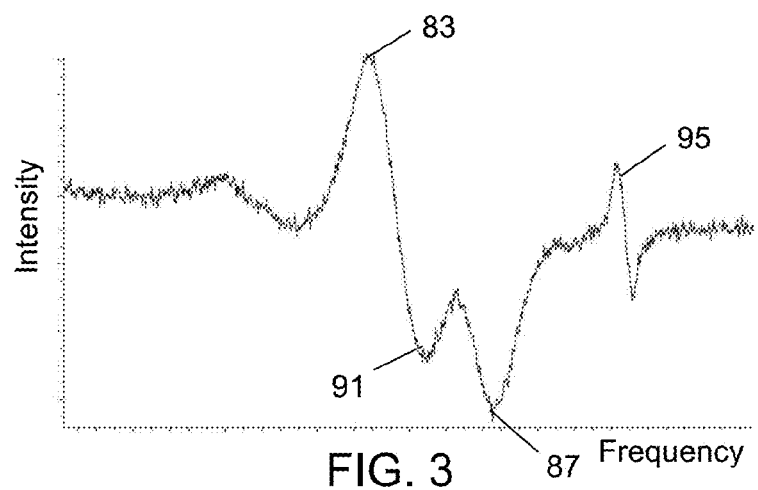
FIG. 3 illustrates resonance intensity versus frequency for a mechanically induced signal in a fingernail sample at low microwave power.
Figure 4:
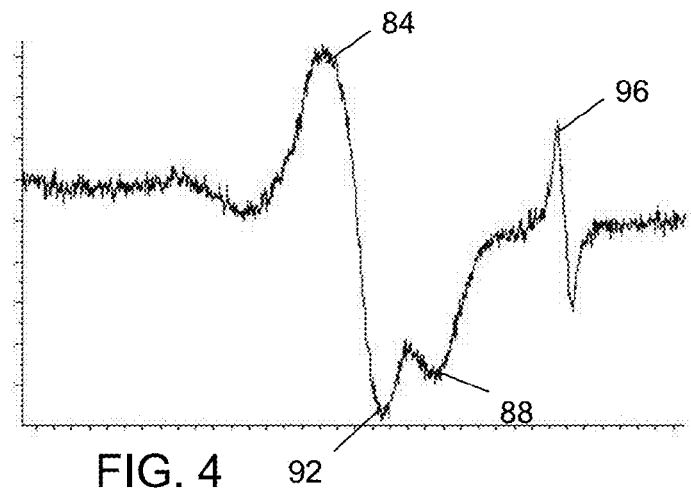
FIG. 4 is a representative illustration of resonance intensity versus frequency for a fingernail sample having both mechanically and radiation-induced signal components taken at low power conditions.
Figure 5:
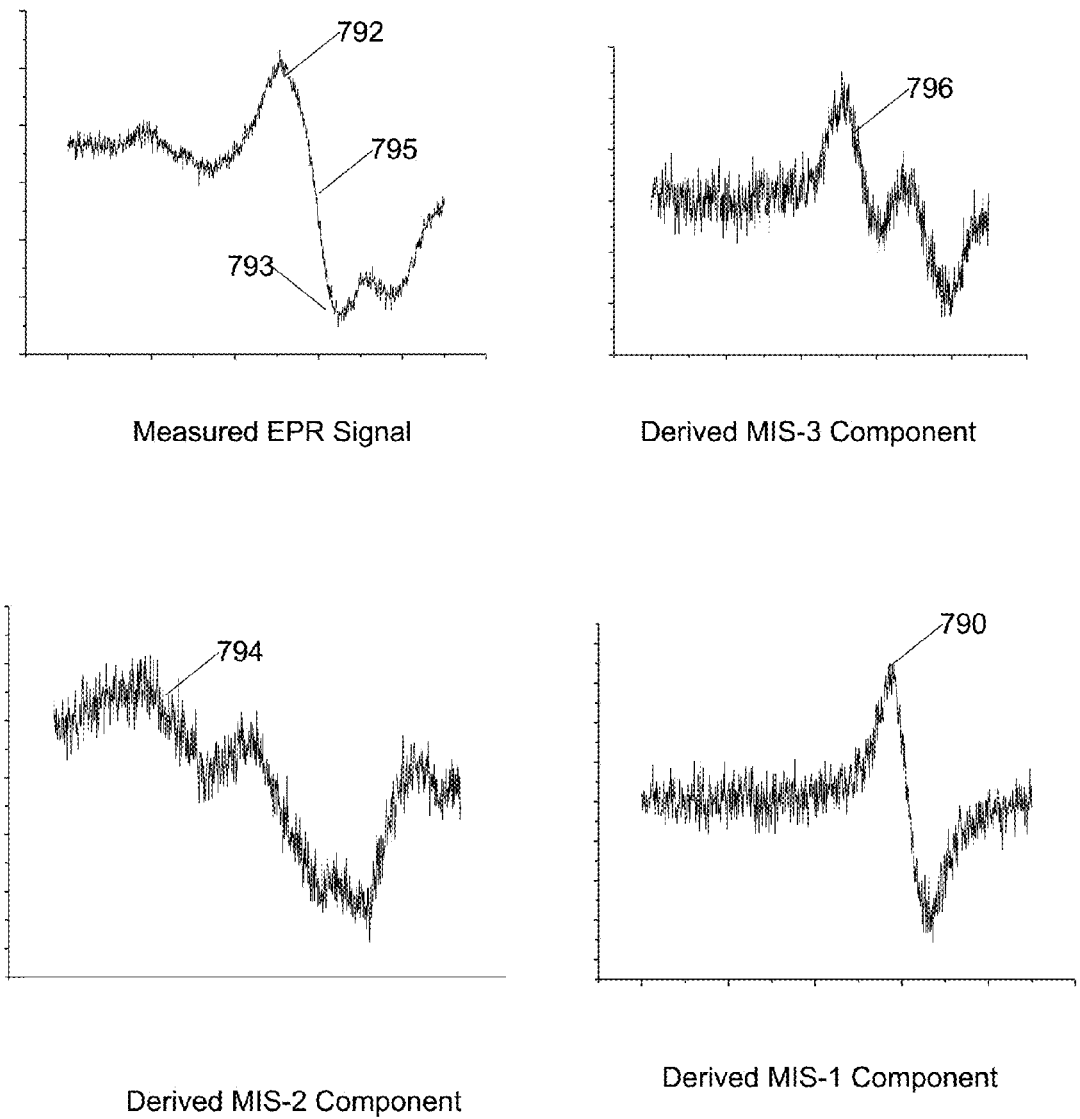
FIG. 5 is an actual composite spectrum of a mechanically induced signal in fingernail clippings, with derived MIS-1, MIS-2, and MIS-3 components extracted therefrom.

FIGS. 2 and 3 illustrate representative mechanically induced signals (MIS) in EPR spectra, FIG. 2 representing the spectra at a high power of three milliwatts, and FIG. 3 at low power of one milliwatt. The intensity of this MIS is quite strong when compared to a radiation induced signal (RIS), or a composite including both radiation-induced and mechanically-induced signal as illustrated in FIG. 4. FIG. 5 also illustrates a mechanically induced spectrum 792 as obtained on a fixed-frequency, scanning-magnetic-field research EPR machine together with separated MIS-1 790, MIS-2 794, and MIS-3 796 components. These spectra often have considerable noise as illustrated in FIG. 5. A radiation-induced signal resembles in many ways that of MIS-1 790 as illustrated in FIG. 5. The crossover region 795, between positive 792 and negative 793 peaks associated with the resonance, of the mechanically induced and RIS components of the signal is of particular interest.

Returning to FIGS. 2-4, in both mechanically induced and composite spectra a low frequency peak 82, 83, 84, a high frequency negative peak 86, 87, 88, and a central negative peak 90, 91, 92 are seen.

In an embodiment, an EPR reference standard such as a manganese dioxide resonance reference sample or a molybdenum compound reference sample is present within the magnetic field while the resonance is being measured. This reference sample provides an additional marker resonance 94, 95, 96, at a frequency or magnetic field different from that of the RIS and MIS signals expected from radiation-exposed fingernail, but at a frequency close enough to provide a calibration reference usable as a reference for both magnetic field intensity or frequency position and intensity of the resonances.

The composite (RIS plus MIS) and mechanically induced spectra resemble each other, and the MIS and RIS plus MIS signals are not distinguishable from intensity or frequency-magnetic field strength combination alone. We therefore process the spectra to extract the RIS component.

It has been found that the MIS signal expected from cutting a human fingernail appears to have at least three components, MIS-1, MIS-2, and MIS-3, in addition to any RIS that may be present. Each component has somewhat different characteristics and is due to a different effect. The MIS-2 component, believed to be due to radicals formed on mechanically disrupted disulfide bonds, has been found not to saturate at high radio-frequency field strengths, increasing as the square root of radio-frequency signal strength. Meanwhile the RIS, MIS-1 and MIS-3 components do saturate. The RIS, MIS-1, and MIS-3 signal levels do not increase as the square root of radio-frequency field strength.

An estimate of MIS-2 signal strength can be derived by measuring the amount by which the overall resonance signal strength increases as RF field strength is increased. The MIS-2 signal component increases as the square root of RF field strength increases at high field strengths, while the remaining components stay at about the same level for incident microwave power between approximately one milliwatt and approximately twenty milliwatts using standard commercial X-band EPR cavities and typical sample sizes.

The EPR resonance spectrometry measurement 56 (FIG. 1) is therefore performed at at least two radio-frequency field strengths in order to determine 58 an MIS-2 component of the EPR spectrum. In an embodiment, low radio-frequency field strength is approximately three milliwatts and high field strength is sixteen milliwatts for cut fingernail sample sizes of twenty-five milligrams.

In another embodiment, low radio-frequency field strength is one milliwatt and high field strength is three milliwatts, as used to generate FIGS. 2-4.

Since it has been found that the MIS-3 component of the MIS signal decays over 30 minutes at temperatures between twenty and thirty degrees Celsius, the sample in its container is held 60 at a temperature in this range for a time sufficient to allow this decay. During this time, EPR spectrometry may be performed on other samples.

Once the sample has been held 60 for a sufficient time to allow the MIS-3 signal to decay, the sample in its container is reinserted into a magnetic field and EPR resonance is measured yet again to give a third measured spectrum 62. The difference between the first measured 56 spectrum and this third measured 62 spectrum is due to the MIS-3 signal, which has now decayed. It has been found that MIS-3 is proportional to another component, the MIS-1 component of the MIS; the MIS-1 signal is therefore estimated 64 based on the difference between the initial EPR resonance measurements 56 and post-delay measurements 62. The RIS is then determined 66 by subtracting the estimated MIS-1 and MIS-2 signal components from the third EPR measurement 62, or by subtracting the estimated MIS-1, MIS-2, and MIS-3 from the first EPR measurements 56. Once the RIS is determined 66, a radiation dose is determined 67 from the RIS.

In an embodiment, an estimated whole-body radiation dose of the individual from whom the samples were clipped is computed from the RIS and compared 68 to triage limits. The estimated dose and triage classification is output 70 in a form suitable for use in determining treatment to be offered to the subject.

In an optional embodiment, in order to provide greater accuracy for treatment purposes as opposed to rough triage screening, the sample is exposed 72 to an incremental, known, amount of radiation. After this incremental exposure 72, the EPR spectrum is measured 74 for a fourth time. The determined 66 RIS is adjusted 76 inversely with the increase in RIS signal in this fourth measurement to compensate for variations in sample size. In this embodiment, the estimated dose and triage classification 68 are determined from this adjusted 76 RIS signal.

Figure 6:
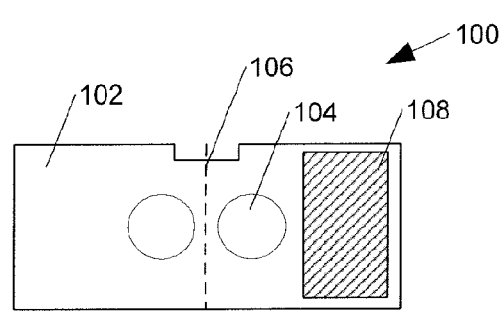
FIG. 6 is an illustration of an embodiment of a sample holder.
Figure 7:
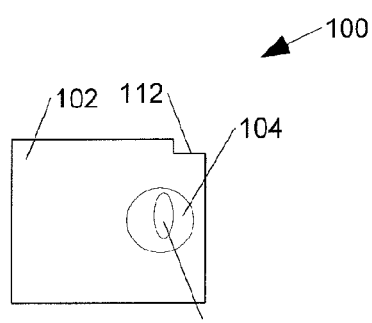
FIG. 7 is an illustration of the sample holder of FIG. 6 closed about a fingernail clipping.

An embodiment of a low-cost clipping holder 100 or clipping container for use with the method of FIG. 1 is illustrated in FIGS. 6 and 7. Clipping holder 100 is made from a rectangular strip 102 of nonmagnetic cardboard or plastic about two inches square having a pair of one-centimeter-diameter holes 104 and a preformed crease 106 for folding. In an embodiment, rectangular strip 102 has a thin sheet of fluorocarbon plastic or a thin, weakly-conductive flexible plastic across, holes 104, and an adhesive area 108 protected by a pull-off sheet (not shown). In a variation of this embodiment, the adhesive area 108 may surround hole 104.

In use, a subject's fingernail is clipped 52 to provide a sample. The sample 110 is trimmed to a standard dimension, typically two by five millimeters, using a trimming punch. The sample 110 is centered on the thin sheet of fluorocarbon or other plastic across one of holes 104, the pull-off sheet is removed from the adhesive area 108, and the rectangular strip 102 is folded along crease 106 to form an approximately square sealed packet or clipping container containing the clipping as illustrated in FIG. 7 in a manner resembling a coin-flip. An alignment notch 112 may be provided to ensure correct alignment in later processing. An upper outer surface of rectangular strip 102 is adapted for recording the subject's identifying information.

Figure 8:
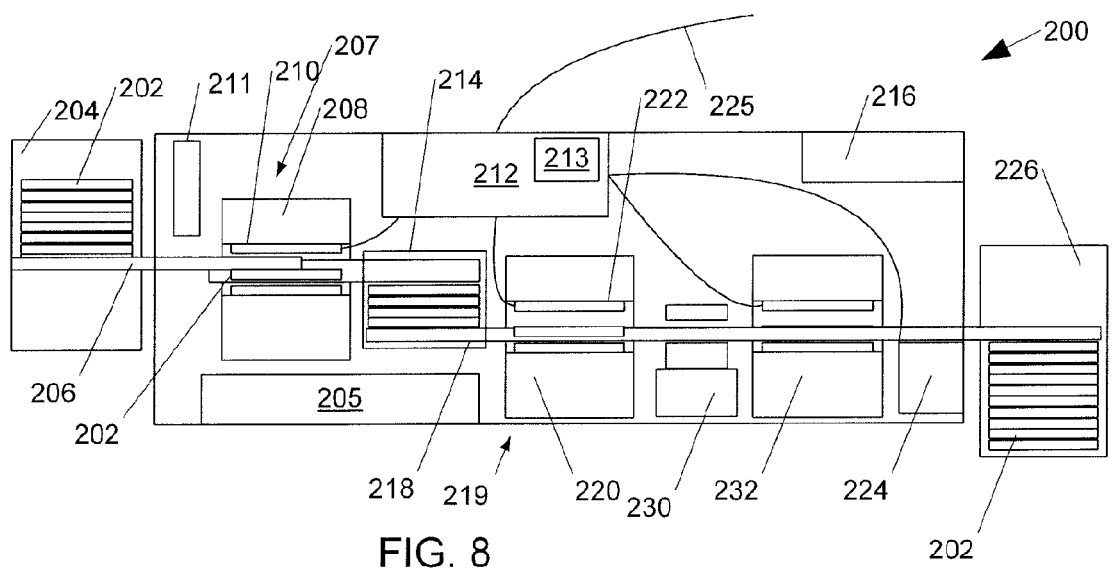
FIG. 8 is a schematic diagram of a sample path for a machine for performing the method of FIG. 1 with the sample holder of FIG. 6.

A machine 200 for performing the method of FIG. 1 is illustrated in FIG. 8. In an embodiment, one or more of each subject's fingernails are trimmed very short, to provide clippings. The clippings are trimmed to a standard size of approximately two by five millimeters. Each clipping is placed in a clipping container 202 such as illustrated in FIGS. 6 and 7. Identifying information, and preferably information of the subject's location during the nuclear event, for each subject is preferably entered into a database computer and a bar-coded identifying label is printed and placed on the containers 202 in a location that does not obstruct hole 104. In an alternative embodiment where additional computers and bar-code label printers are unavailable, identifying information is written directly on the containers 202. In an embodiment where a database computer is available, the subject's location at the time of the event is entered into the database along with subject's identifying information.

Once labeled the containers 102 are placed in a removable magazine 204. Clipping containers 202 and magazine may be stored 204 at a low temperature. Clipping containers 202 are preferably maintained at low temperature, such as minus ten Celsius, until they are fed individually by shuttle 206 into an EPR measurement position 207 where the holes 104 are centered between poles of, and within the magnetic field of, a magnet 208 and adjacent to a radio-frequency (RF) coupling coil 210 or radiator. As the clipping containers enter machine 200 enroute to the EPR measurement position, the bar-coded identifying label is read by a bar-code reader 211, subject identity is stored in electronics 212 in memory of a processor 213. Alternatively, clipping containers 202 may be fed into the EPR measurement position within five minutes of clipping the fingernails.

Shuttle 206 is driven by an actuator 205. RF generator, measuring apparatus, and processor 212 (hereinafter electronics 212) is connected to the coupling coil 210 or other radiator for applying RF to the clipping in the clipping container. Electronics 212 controls the actuator 205 or actuators required to operate each shuttle 205, 218 of the machine. The RF generator, measuring apparatus, and processor 212 then measures 56 the EPR spectra of the sample at at least a low and a high power setting to determine 58 the saturable MIS-2 component of the EPR spectra. The electronics 212 may sweep either the radio frequency or, using a trimming coil, the magnetic field past a resonant frequency-field strength combination to derive each EPR spectrum. In an embodiment, the magnetic field has constant intensity across the holes 104, the thin plastic covering the hole 104, and the sample 110, but has a gradient outside this area so that resonances due to contaminants in the outer portion 102 of the holder are outside the frequency range of EPR spectra of the sample. In an embodiment, the magnet 208 is a permanent magnet. In an alternative embodiment, magnet 208 is a permanent magnet supplemented by one or more electromagnets for making adjustments of less than ten percent in magnetic field strength and field gradients.

The clipping container 202 is then transferred by shuttle 206 into a holding area or bay 214. The machine 200, and in particular holding area 214, is maintained at a predetermined temperature of between twenty and thirty degrees Celsius by temperature controller 216. This temperature is chosen such that the MIS-3 component of the EPR spectra will fully or partially decay while the clipping container 202 remains in holding area 214.

A second shuttle 218 then transfers the clipping container 202 to a second EPR measurement position 219 where the holes 104 are centered between poles of a magnet 220 and adjacent to a second radio-frequency (RF) coupling coil 222. Electronics 212 measures the EPR spectrum 62 a second time, and computes 66 the RIS as above described. Eventually, the clipping container 202 passes over an inkjet printer device 224 where estimated radiation dose information and triage category are printed, under control of electronics 212, onto a bottom surface of the container 202. In an alternative embodiment, estimated radiation dose is printed on the container 202 in both human readable form and in machine readable form as a bar-code.

The identifying information read by bar-code reader 211 when the container 202 entered the machine, together with the estimated radiation dose information and triage category, are combined into a patient record and reported to a database computer (not shown) through a 10/100 Base-T network connection 225 or other datalink if a database computer is available; if no database computer is available, several hundred patient records may be stored in electronics 212. The container 202 is then transferred by reciprocating shuttle 218 into an output bin 226, which may, but need not, be a duplicate of magazine 204.

In an alternative embodiment, a belt is used to transfer the clipping containers 202 instead of a reciprocating shuttle 218.

In an alternative embodiment of the machine 200, as illustrated in FIG. 8, between second EPR measurement position of magnet 220 and printer 224, the clipping container 202 passes over calibrated radiation source 230. Radiation source 230 may be a cesium source, an electron beam source, or another source of ionizing radiation. Once irradiated incrementally 72 by radiation source 230, clipping container 202 passes through a third EPR measurement position of magnet 232, where electronics 212 measures the EPR spectrum again 74. Electronics 212 thereupon uses the difference in EPR spectra due to the increased radiation-induced signal to adjust 76 its computed pre-increment RIS, dose, and triage category accordingly—among other effects that can be adjusted in this manner are mass differences in the fingernail sample.

Once printed and transferred into output bin 226, the container 202 may be disposed of in full-electronic recordkeeping environments. In the event communications are disrupted and electronic recordkeeping is unavailable—as is likely following a nuclear attack—the container 202 having a sample from a particular subject may be given as a record to that subject if sent home because of triage as likely a worried-well subject or a subject exposed so lightly that no immediate treatment is needed—the subject may show the container 202 with the information printed on it to her private physician should problems develop.

With subjects triaged into categories requiring treatment, or being treated for other injuries, the container 202 may have a hole punched in a corner so it may be suspended from a cord tied around the subject's wrist, ankle, or neck so its dosage and radiological triage information is available with the subject regardless of where the subject is transported to or of communication difficulties between machine 200 and the hospital ward wherever the subject is transported to. In an alternative embodiment, a gummed label or sticker is printed with the identifying, triage, and dosage information and may be attached to a separate triage card that is attached to the subject—in an embodiment the triage card is suspended from a string tied around the subject's neck.

Figure 9:
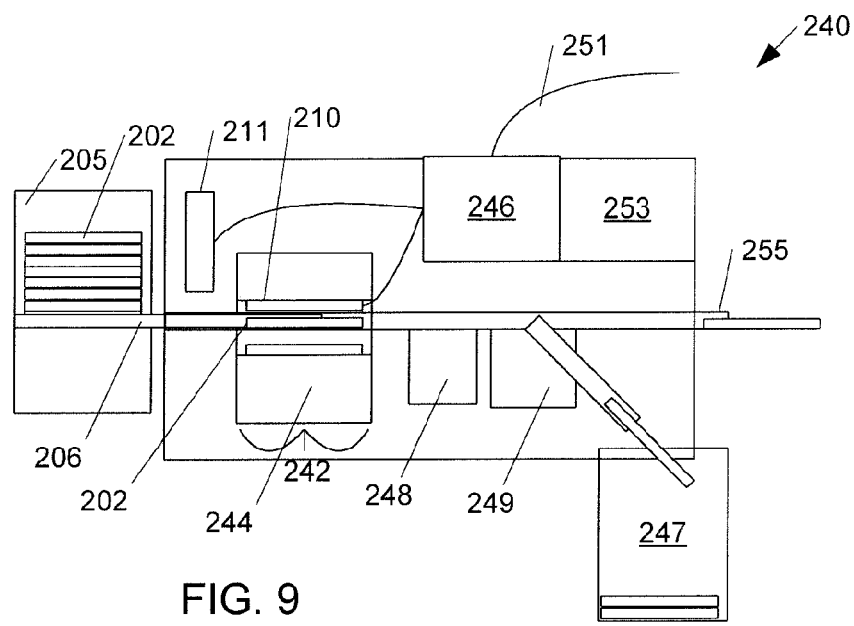
FIG. 9 illustrates an alternative machine for prescreening samples for significant doses, and which is adaptable to feed the machine of FIG. 8.
Figure 11:
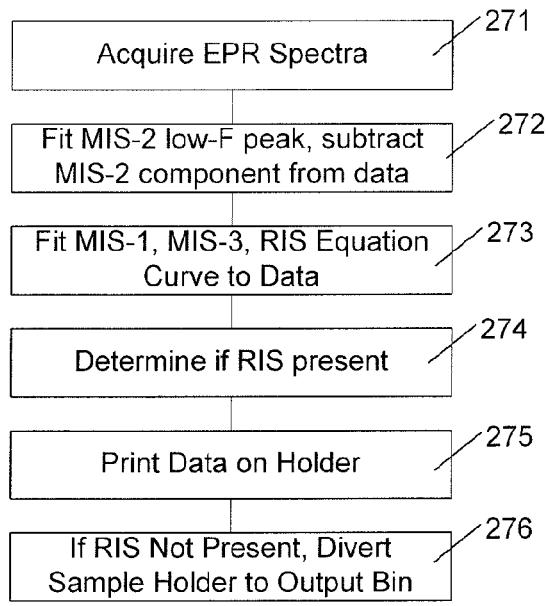
FIG. 11 illustrates operation of a screening device of FIG. 9.

FIG. 9 illustrates a simplified machine 240 suited for rapid initial screening of subjects, and which operates according to the method of FIG. 11. As with the machine of FIG. 8, chilled fingernail-clippings in sample-holders 202 are fed into the machine 240 by reciprocating shuttle 206 from a magazine 205. The sample holders 202 pass under a bar-code reader 211 where identifying information is read to electronics 246, and into an EPR measurement station 242 having magnet 244, and pickup coil 210 or radiator connected to measurement and processing electronics 246.

With reference to FIGS. 2-4, EPR spectra for MIS alone have a somewhat flattened low frequency peak 83, 84, when compared to a composite RIS-MIS signal 85. Further, EPR spectra for MIS have somewhat weakened central peak 90, 91 when compared to composite RIS-MIS signals 92 of nearly equivalent high frequency peak 86, 87, 88, strength. These differences occur because the RIS peak superimposes a signal on the low frequency peak 83, 84 and central peak 90, 91, but does not have a component in the region of the higher frequency peak 87, 88, 89.

Figure 10:
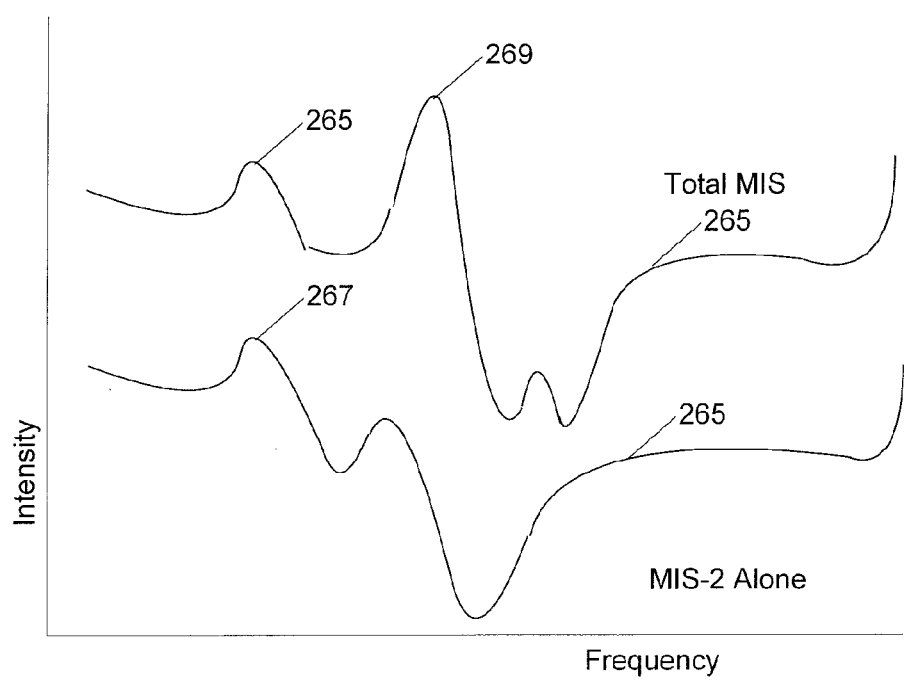
FIG. 10 illustrates a peak of MIS-2 separated from the peaks of MIS-1, MIS-3, and RIS.

With reference to FIG. 10, it has been observed that a pure MIS-2 signal 265 has a low-frequency MIS-2 peak 267 that is at a lower frequency or field than low frequency/field peak 83, 84, 269 of a composite MIS-RIS Signal (FIG. 4). Further, the RIS, MIS-1 and MIS-3 signals do not overlap this low frequency MIS-2 peak 267. This low frequency/field MIS-2 peak 267 can thus be measured by fitting this portion of the spectra to expected responses of MIS-2 alone. The measurement of MIS-2 is multiplied by expected responses of MIS-2 alone to determine an MIS-2 component of the spectra at low frequency peak 83, 84, central peak 90, 91, and high frequency peak 87, 88, 86; this is then subtracted from the spectra to produce a spectra with MIS-2 removed.

MIS-1, and MIS-3 are not always proportionate to MIS-2.

Measurement and processing electronics 246 acquires rapid EPR spectra 271. Processing electronics 246 locates the peaks of the spectra with MIS-2 removed by examining the spectrum at a known frequency distance from the reference peak 94, 95, 96 which can be paramagnetic states of molybdenum or manganese or another suitable substance positioned in the field, estimating MIS-2, and subtracting 272 the MIS-2 component from the data. Of these common reference molecules, molybdenum is preferred because it does not have a peak that would interfere with recognizing the lower frequency peak of MIS-2 and can be present in the field along with the sample. A curve-fitting algorithm based upon expected spectral responses of MIS-1, MIS-3, and RIS is used to determine parameters for an equation to best fit 273 the acquired EPR spectra with MIS-2 removed. Parameters of the fitted equation are then used to determine 274 whether a significant RIS is present. For example, a ratio of relative heights of the central peak 90, 91, 92 as measured by curve-fitting and the high frequency peaks 87, 88, 86 may be compared against limits to determine if an RIS is present.

The sample holder is further transferred by reciprocating shuttle 206 through printer 248 where triage information may be printed 275 on holder 202, and a solenoid 249 operates a diverter. If no significant RIS, or a very light RIS consistent with radiation doses from which a subject should recover without treatment, is present, the holder 202 is diverted 276 and drops into a light or no-dose output bin 247. If presence of a RIS is detected, the holder 202 is passed through a second output 255 into magazine 204 of the more precise dose measurement and triage system of FIG. 8.

The rapid initial screening machine of FIG. 9 is held at a temperature just above freezing by refrigerator 253 to slow decay of MIS-3 and thereby to avoid corrupting data measured by the following, more precise, machine of FIG. 8. Testing records containing identifying information from bar code reader 211 and measurements are transmitted to any attached database computer over network cable 251.

Figure 12:
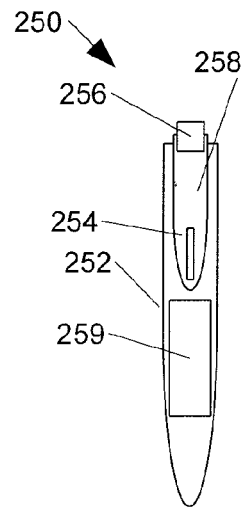
FIG. 12 illustrates an alternative tubular sample holder.

In an alternative embodiment of the system, a tubular sample holder 250 as illustrated in FIG. 12 is used. This holder has a tube 252 that may be made of quartz or another material that does not have substantial EPR. The sample 254 is trimmed to an appropriate standard size and placed within tube 252, and sealed in place with an elastomeric plug 256. Also present in the holder 250 is an EPR reference sample 259.

Figure 13:
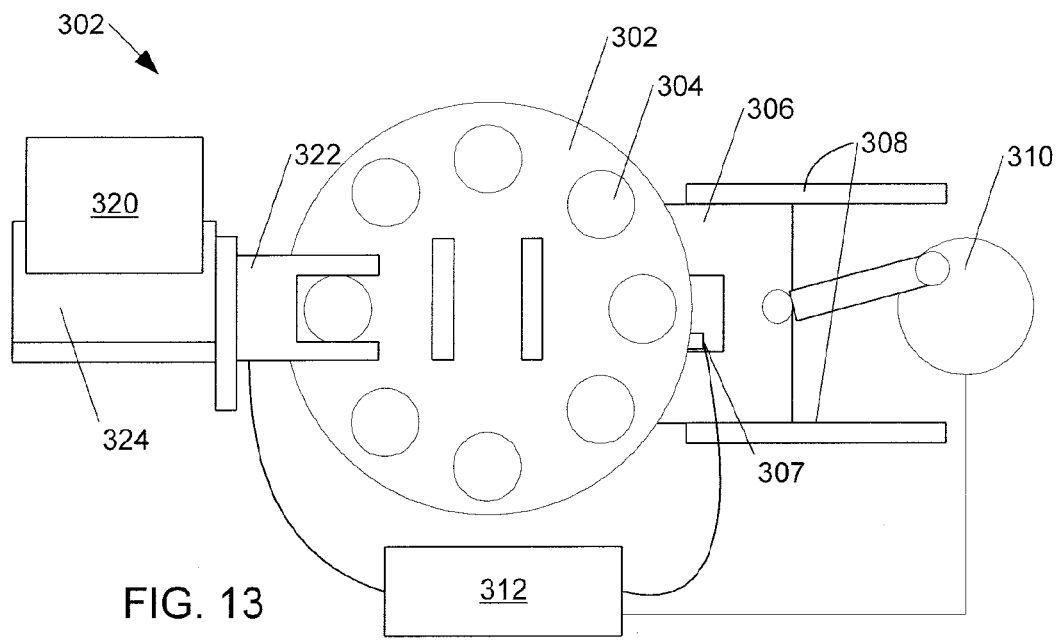
FIG. 13 is a schematic diagram of a machine for performing the method of FIG. 1 with the sample holder of FIG. 12.

The tubular sample holder 250 is used with a machine 300 having a removable circular magazine tray 302 (FIG. 13) having several numbered holes 304 for holding sample holders 250. Samples in sample holders 250 are manually placed in holes 304 of tray 302 and the tray is inserted into machine 300. Magnet 306 and coupling coil 307 are mounted on a reciprocating mount on rails 308 and driven by actuator 310; to perform an EPR spectrum measurement, electronics 312 directs actuator 310 to extend magnet 306 and coil 307 to a position as shown surrounding tube 250 as tube 250 hangs below a hole 304. Upon completion of a measurement, such as measurements 56, 62, 74, the electronics 312 directs actuator 310 to retract magnet 306 into a retracted position (not shown) such that magazine tray 302 may rotate to bring another sample holder 250 in another hole 304 into position for measurement. Electronics 312 tracks measurements by tube position.

With sample holder 250, in order to prevent artifacts from radiation-induced EPR of the tube, when incremental irradiation by a calibrated radiation source 320 is desired, a tube-flipper 322 arm grasps tube 250 by its rim 258 and inverts it while placing only a portion of tube near rim 258, into an irradiation position 324. The sample 254 falls by gravity into this exposed "top" portion of the tube, and when reinserted by flipper 322 into magazine tray 302 after irradiation, the sample falls back into a lower, non-irradiated, portion of the tube. Once all tubes in a magazine 302 are fully processed, a report including triage information is generated and magazine 302 may be removed.

In an alternative embodiment, once it has been determined that a subject has received at least some radiation, fingernail and toenail clippings from each hand and foot are analyzed separately according to the method of FIG. 1 to determine a dosage distribution across the body. Dosage distribution is of interest because bone marrow from lightly or un-irradiated limbs may provide stem cells to re-seed marrow in more intensely irradiated portions of the body, therefore identifying subjects who have received exposures that vary from limb to limb may allow some of these unevenly-irradiated subjects to avoid drastic treatments like heterologous bone marrow transplantation.

In large-scale disasters, subject's recalled history alone has proven to not always be a good indicator of exposure to toxic or radioactive materials and corresponding need for treatment. Similarly, apparent physical injuries and symptoms are not good indicators of intensity of radiation doses received by a subject. When a radiation disaster, whether by accident like Chernobyl, or weapon like Hiroshima, happens, medical care systems will likely be overloaded. With both machines, to best use available resources, the triage information is used to quickly sort (or triage) potential victims into categories of:

a. those who are unexposed or exposed below the detection threshold of the system.
b. those who have received detectable doses of radiation, but these doses are small enough that they will probably recover without need for treatment for acute radiation sickness;
c. those who have received significant doses requiring conventional, conservative, treatment, for radiation sickness; which may include transfusions of blood products, prophylactic antibiotics, nursing care, and nutritional support;
d. those who can possibly be saved by aggressive treatment such as bone marrow transplant; and
e. those who will die despite any reasonably available treatment, and to whom hospice therapy may be offered.

Typically, emergency workers are trained to tie a color-coded triage tag to each victim assessed during a large-scale disaster. Typically, green is used to indicate those who will survive without immediate treatment—these may wait many hours for evacuation or further assessment or may be sent home depending on circumstances, yellow for those who need some near-term care but are not in critical condition—these may wait for transportation or treatment but not as long as those coded green, red for those who require immediate treatment to survive and who receive priority transportation or treatment, and black for those who are expected to not survive even if given the best available treatment. Preprinted triage tags with perforated tear-strips for removing colored regions are often provided for use in such situations. Each tag has red, green, yellow, and black—colored regions and white space for other information; when attached to a victim the colored regions distant to the colored region of color appropriate to that victim are removed by emergency medical personnel by tearing along the perforations. Other systems of tags may provide color-coded stickers for attaching to tags. Victim identity, assessment of injuries, and other information may be written in the white spaces. Once patients are tagged, they are evacuated and/or treated in order of priority.

In an embodiment, the fingernail dosimeter of FIG. 8, 9, 13, 14, or 15 is equipped with a printer for printing a radiation-dose and radiation-triage sticker for attachment to a backside of a triage tag that is in turn attached to the subject. The front side of the triage tag is filled out with assessment, medication, and treatment information regarding other injuries the subject may have received, and the appropriate tear-strips are removed. In an alternative embodiment, estimated radiation dose is printed on the sticker in both human readable form and in machine readable form as a bar-code.

In an alternative embodiment, a single EPR spectrum is measured before the delay, and two EPR spectra at different electromagnetic field intensities are obtained after the delay. The components of the mechanically induced signal are obtained similarly to the method of FIG. 1, with the MIS-2 component being determined from differences between the two post-delay spectra.

Figure 14:
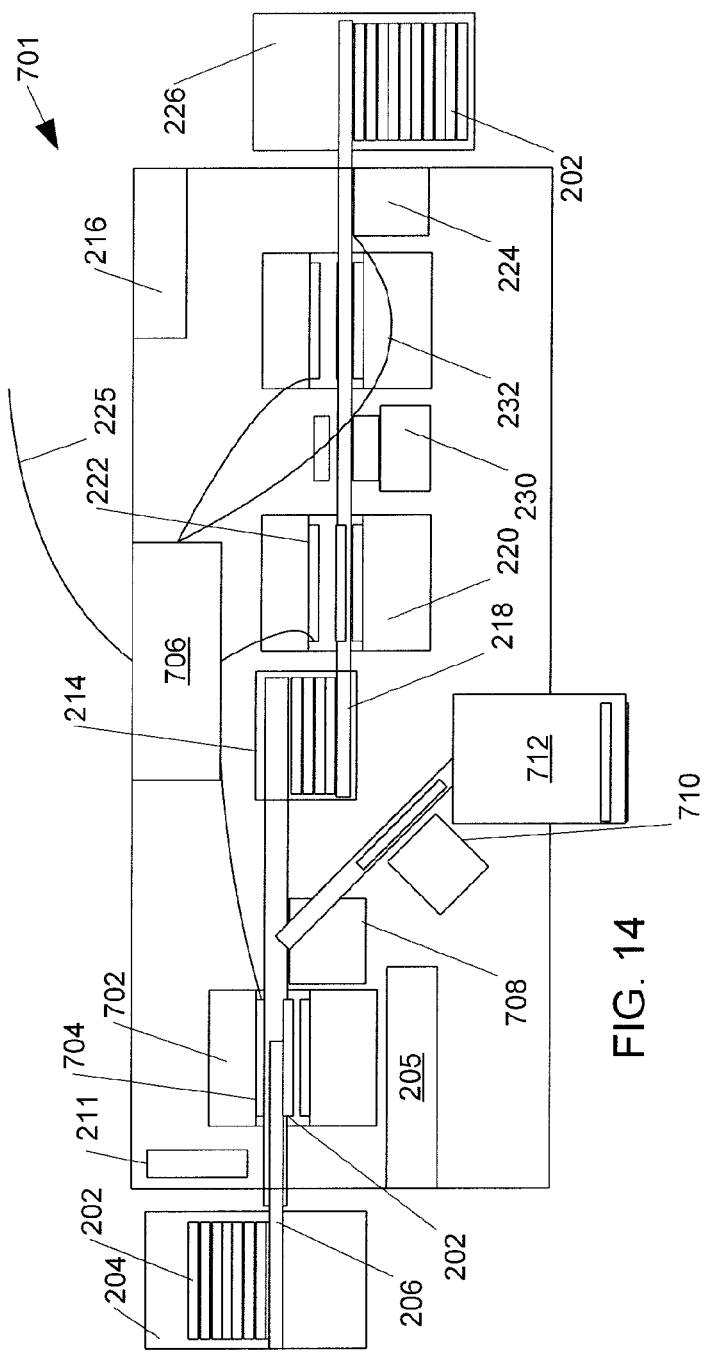
FIG. 14 is a schematic diagram of a machine for performing both rapid triage and quantitative measurement of radiation exposure.

In an alternative embodiment of a machine 701 resembling that of FIG. 8, as illustrated in FIG. 14, the machine feeds sample-holders 202 to a first EPR measurement station in the manner previously discussed with reference to FIG. 8. At the first measurement station, having magnet 702 and pickup coil 704 operating under control of electronics 706, a first EPR spectra is obtained, stored, and processed as described above with reference to FIG. 11. If this provides indication that little or no radiation exposure has been received, electronics 706 operates a diversion solenoid 708. If diversion solenoid 708 operates, sample holder 202 moves past printer 710 into output bin 712. Printer 710 prints exposure and triage information on the sample-holder 202 and optionally on a triage-tag sticker printer (not shown); this information is also transmitted over network cable 225.

In the event that a significant exposure is detected, the machine of FIG. 14 immediately obtains a second EPR spectrum at a second RF field power level. The second EPR spectra and stored first EPR spectra are processed as previously discussed with reference to FIG. 1 and FIG. 4; when acquisition of the second spectra is complete the sample holder 202 is advanced into holding area 214 as previously discussed with reference to FIG. 8, the sample holder is then held at a predetermined temperature in this holding area 214 for half an hour and advanced to a second EPR measurement station as previously discussed with reference to FIG. 8.

In the embodiment of FIG. 14, approximately twice as many sample-holders 202 may be processed in an hour than with the machine of FIG. 8 because the majority of samples processed in a mass-disaster event are expected to be from subjects who do not need treatment for acute radiation syndrome, and in these samples only one spectrum is needed.

Figure 15:
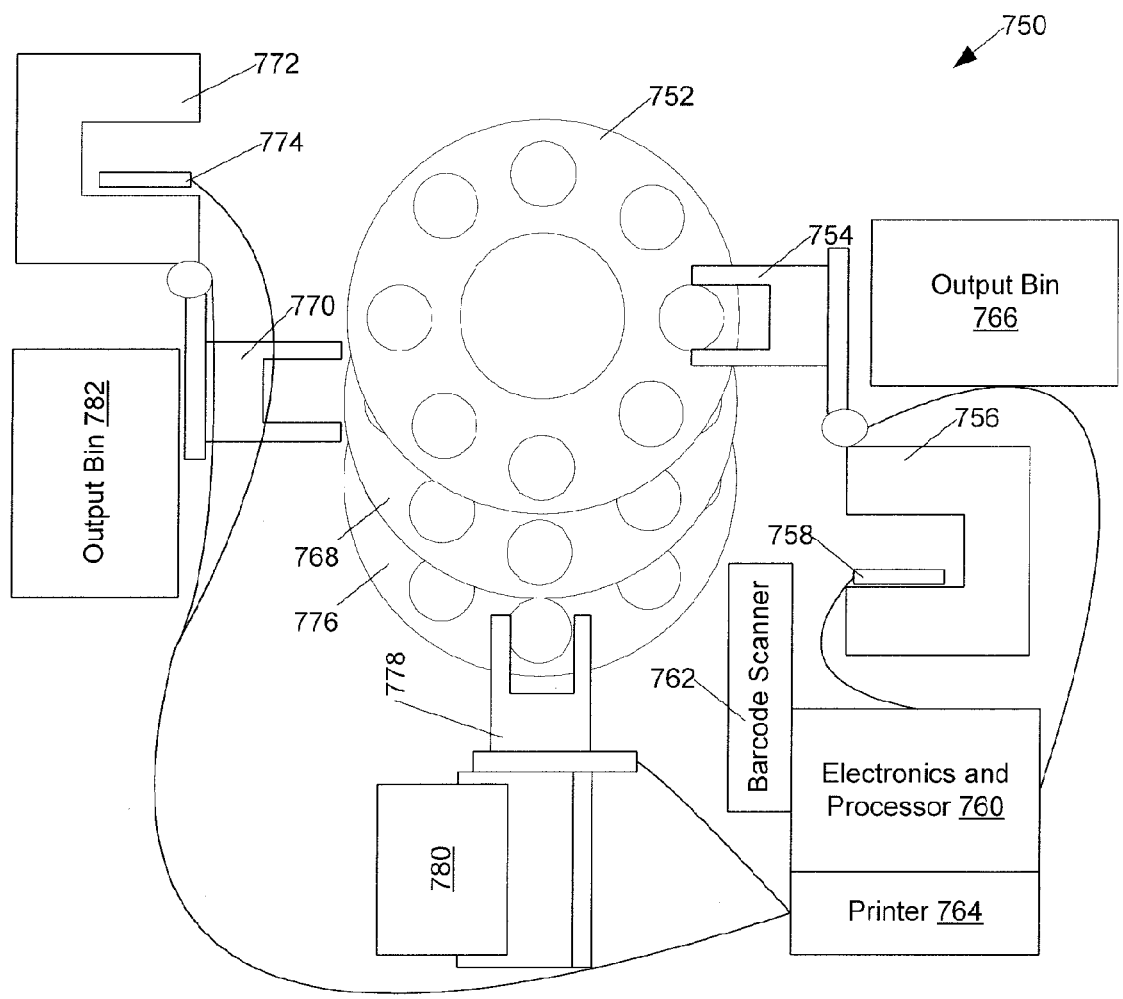
FIG. 15 is a schematic diagram of an alternative embodiment of a machine for performing rapid triage and quantitative measurement of radiation exposure.

In the alternative embodiment 750 of FIG. 15, samples are held in a sample container 250 such as tube 258 of FIG. 12. These sample containers 250 are place in sample holders 252 and are placed in a circular magazine tray 752 that is refrigerated to avoid MIS signal degradation. Electronics and processor 760 directs rotation of magazine tray 752 until earlier samples are processed and manipulator 754 can grasp the sample holder. The sample holder is then passed in front of barcode scanner 762 to read identifying information from a label on the sample holder and placed in a first EPR measurement station between poles of magnet 756 and adjacent to pickup coil 758. Pickup coil 758 is then used by electronics and processor 760 to acquire a first EPR spectrum. The EPR spectrum is then processed by processor 760 as previously described with reference to FIG. 11 to determine an RIS, and estimated dose, and a raw triage category. If it is found that the estimated dose is unequivocally low or none, an appropriate record of the identifying information and measurement is sent to a database computer and printed on printer 764, and manipulator 754 places the tube in an output bin 766.

If the estimated dose is moderate or high, or if the measurement is uncertain, a second EPR spectrum is obtained at a second power level, in accordance with the method of FIG. 1, and the manipulator 754 is placed into a second magazine tray 768 maintained at between twenty and thirty degrees Celsius. When magazine tray 752 is emptied, an alarm is sounded so human attendants can refill magazine tray 752 with any further sample holders having samples needing testing.

After residing in second magazine tray 768 for half an hour or more, and the magazine tray 768 rotates to an appropriate position, second manipulator 770, grasps the sample holder and inserts it into second EPR measurement station having magnet 772 and pickup coil 774. Pickup coil 774 is then used by electronics and processor 760 to acquire a third EPR spectrum, and the sample holder is replaced in third magazine tray 776 as determined. The magazine tray 776 then rotates to an incremental exposure station where sample flipper 778 grasps the sample holder, inverts it, and exposes it to radiation source 780, once exposed the sample holder is re-inverted and returned to magazine tray 776. Magazine tray 776 rotates again until second manipulator 770 can grasp it and re-insert it in the second EPR measurement station where the fourth EPR spectrum is obtained. The first second, third, and fourth spectra are processed according to FIG. 1 to generate a final computed RIS, a final radiation dose, and a final triage category—this data is printed on printer 764 with identifying data, and a record containing this information is transmitted to any associated database computer. Manipulator 770 then places the sample holder in a second output bin 782.

Figure 16:
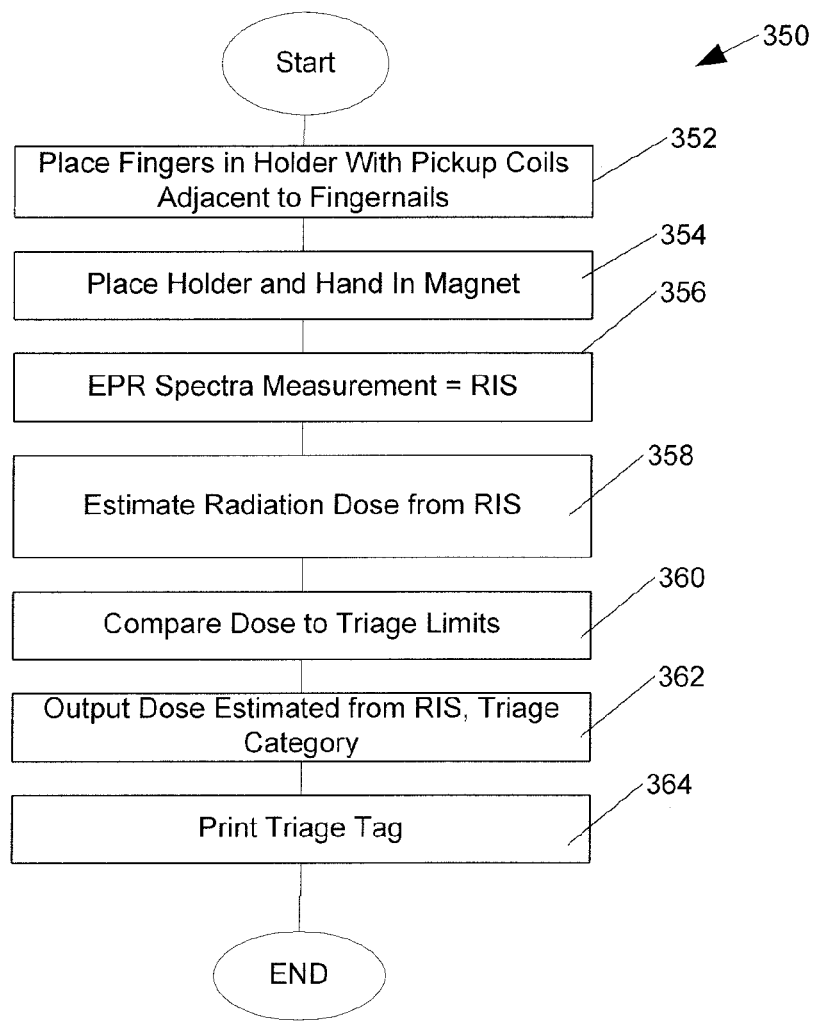
FIG. 16 is a flowchart of a rapid triage method wherein radiation exposure is detected by in-vivo measurements of EPR spectra in fingernails.

Radiation-induced EPR spectrum components (RIS) in fingernails and toenails may also be detected in vivo, according to the method 350 of FIG. 16. This eliminates generation of the MIS signals intrinsic to the process of clipping, and may provide more accurate results. Further, this permits excluding residual MIS signals from fingernail edges cut during pre-exposure normal grooming by placing the coils on a more proximal portion of the fingernail. In this method 350, a subject's hand is placed 352 in a holder such that pickup coils are retained adjacent to the dorsal surface of the fingers adjacent to the fingernails. The pickup coils are preferably positioned sufficiently proximal to the ends of the fingers that no mechanically-induced signal from recent clipping of the fingernails will be detected, yet sufficiently distal that the coils are adjacent to fingernail and not skin. The pickup coil has the property that its electromagnetic field interacts primarily with the fingernail and not the nailbed, thereby making it feasible to use high frequency EPR in vivo. The subject's hand is then placed 354 between the poles of a magnet. A RF measurement and processing system then measures 356 the radiation-induced EPR signal (RIS) from the fingernails, and uses a precomputed calibration curve to estimate 358 an estimated whole-body radiation dose of the subject based on the RIS EPR signal and assuming even irradiation of the subject. Should the subject lack or have injuries to her hands, or should limb-differential radiation dose information be desired, the subject's toenails are used in place of, or in addition to, the fingernails.

The estimated radiation dose is compared 360 to triage limits, and radiological triage information is output 362 by a display system to a system operator. A radiological triage tag may also be printed 364. Some events likely to cause large numbers of radiological injuries, such as nuclear attack, are also likely to cause non-radiological injuries such as burns, fractures, abrasions, and lacerations. The radiological triage information is then used, together with assessment of non-radiological injuries the subject may have sustained, to assist triage personnel in determining whether and what kind of treatment is offered to the subject.

Figure 17:
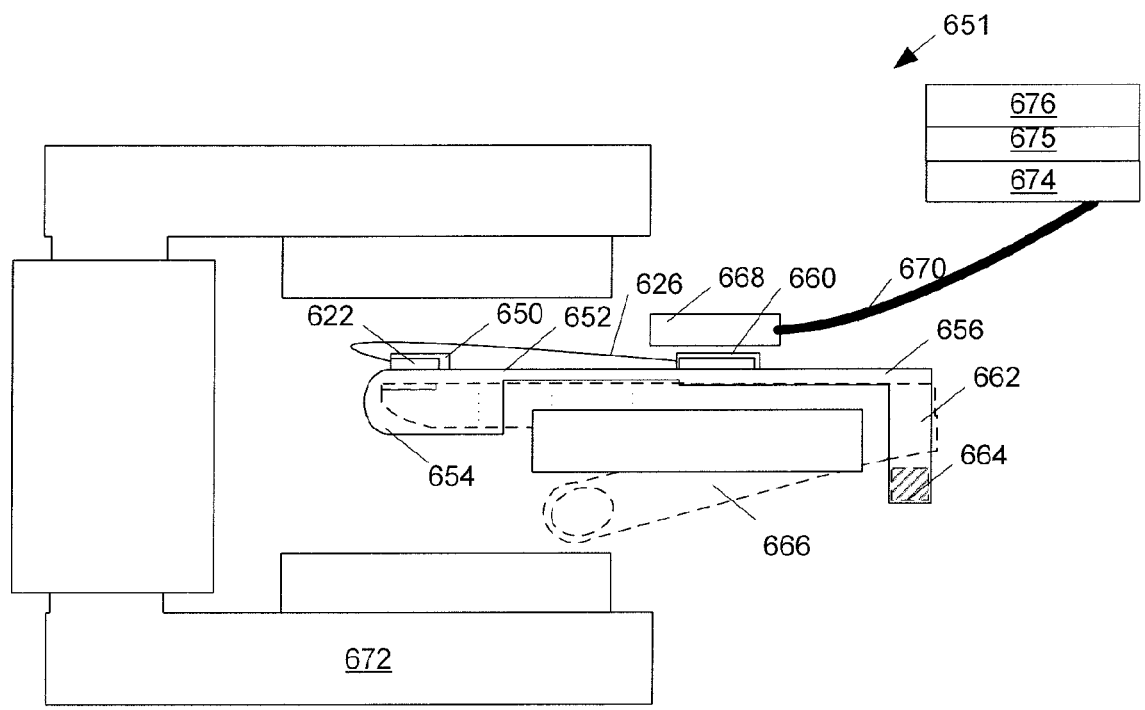
FIG. 17 is a schematic diagram of a device for holding coupling coils adjacent to the fingernails for EPR measurements.

A particular embodiment of a holder for retaining pickup coils in position on the dorsal surface of a subject's fingers is illustrated with apparatus 651 for measuring the EPR resonances of the fingernails in FIG. 17.

This alternative embodiment has a resonator 620 (FIG. 21) having from two to five plastic chips 622 cast from a flexible plastic and containing pickup coils 624 that will conform to the curvature of the top of a subject's fingernails. In an embodiment, a small sample of an EPR standard material 623 may also be embedded in the plastic chip 622. The pickup coils 624 in the plastic chips 602 are coupled by transmission line portions 626 and 628 to a coupling coil 630. In an embodiment, transmission line portions 626 are coaxial cable portions, in an alternative embodiment, transmission line portions 626 are twisted-pair portions, and the pickup coils 624, transmission line portions 626, and coupling coil 630 are formed from a single, larger, insulated, twisted wire loop.

Figure 21:
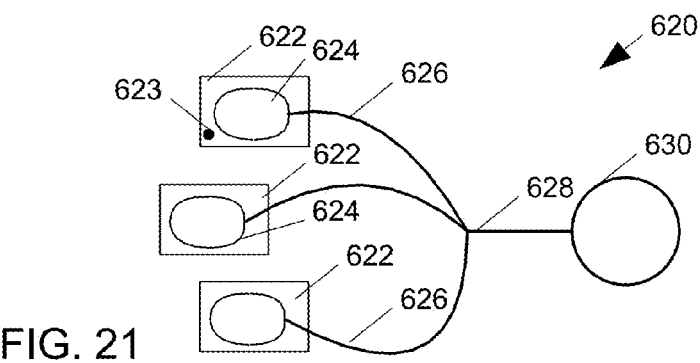
FIG. 21 is a top view of a sensing loop device suitable for sensing EPR spectra in enamel of the teeth and/or keratin of the fingernails.

The plastic chips 622 of the resonator of FIG. 21, with pickup coils 624, typically comprising one or two turns of copper wire, are inserted into pockets 650 (FIG. 17) in the dorsal surface of finger cups 654 of a thin elastomeric partial glove 652 having two to five finger cups 654 attached by elastomeric straps to a backhand portion 656 positionable above the back of the subject's hand. The glove 652 holds the plastic chips 622 near, and above, the subject's fingernails when the subject's fingertips are inserted into the finger cups 654 such that the pickup coils 624 are adjacent the dorsal surface of each fingertip and the pickup coils 624 are adjacent the subject's fingernails. In an embodiment, the elastomeric partial glove is made as a single piece from silicone rubber. The pickup coils 624 are connected by transmission sections 626, 628, to a coupling coil 630 that is inserted into a pocket 660 of the backhand portion 656. A wrist strap 662 having a hook and loop fastener 664 serves to secure the partial glove 652 to a subject's hand 666.

The hand, wearing the partial glove 652, is then inserted between poles of the magnet 672 and coupling coil 610 is held close to a second coupling coil 668 that is in turn connected by a coaxial transmission line 670 to apparatus 674 for measuring a radio-frequency EPR spectrum. As with the other embodiments herein described, the resonances measured are fed to a processing system 675 for determining an estimated radiation dose from the spectrum, and a printer 676 for printing a triage tag or sticker, The second coupling coil 668 is magnetically coupled to the coupling coil 610 of the resonator and permits the apparatus 674 for measuring a radio-frequency resonance to measure EPR resonances of the fingernails. The EPR spectrum is measured and an approximate whole-body radiation dose is calculated therefrom according to the method of FIG. 16 or as otherwise described herein.

The coupler having pickup coils 624 of from one to two turns of copper wire in the plastic chips 622, coupled by twisted-pair transmission line portions 626 and with a coupling coil 630 operates in a magnetic field of about 400 gauss with resonances at approximately 1.2 gigahertz. This embodiment may also operate at some higher frequencies.

The device of FIG. 17 has advantage in that it is self-adjusting for many different lengths and diameters of a subject's fingers, and widths of the subject's fingers, hands and wrists because the silicone rubber elastomeric material stretches to accommodate fingers of various sizes.

Figure 18:
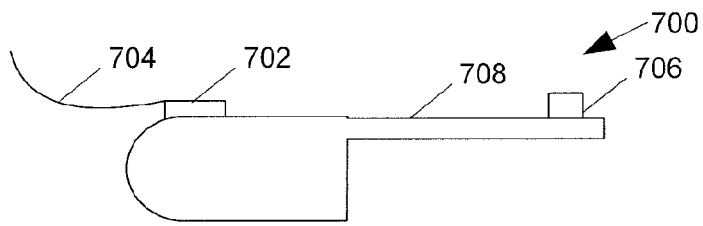
FIG. 18 illustrates a device having finger-cups for holding coupling coils adjacent to the fingernails for EPR measurements

In an alternative embodiment, three finger-cups 700 as illustrated in FIG. 18 are used, one for each of the index, second, and ring fingers of a subject's hand. Each finger cup 700 has a pickup coil 702 in position such that it will center over a subject's fingernail when a finger is inserted into the finger cup 700, the coil 702 is attached by a flexible cord 704 to RF measurement electronics. The finger-cup 700 also has apparatus, such as a button 706 or screw-hole in an elastomeric strap 708 for securing it to a machine. Elastomeric strap 708 permits self-adjustment for some variations in finger lengths.

Figure 19:
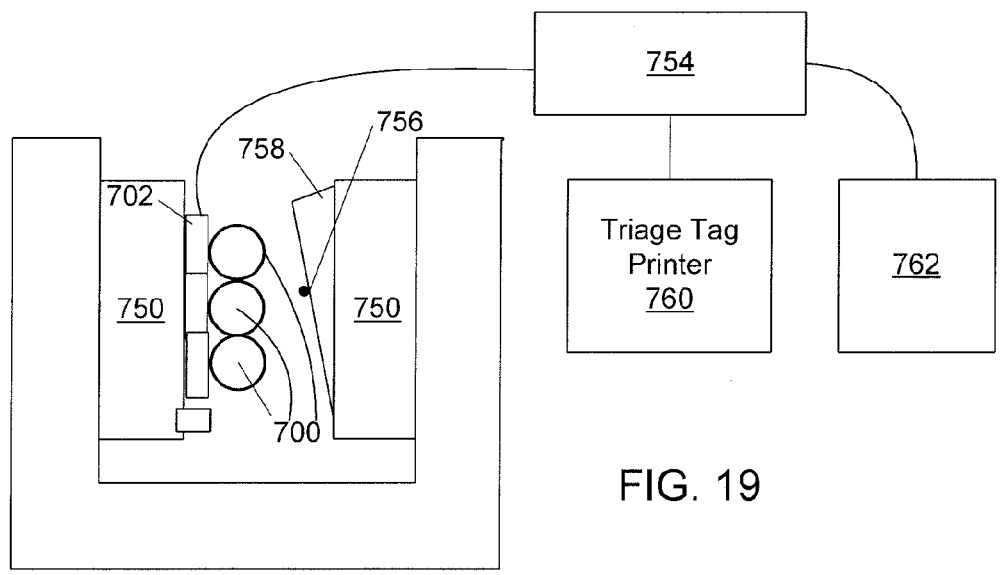
FIG. 19 is a schematic diagram of a machine for performing EPR measurements from fingernails.

The three finger cups 700 are attached to and suspended between poles 750 of a magnet (FIG. 19) with pickup coils 702 connected to the RF measurement and computing electronics 754. A reference 756 containing a standard such as manganese dioxide or a molybdenum compound is also present between the poles 750. A subject is invited to place an appropriate number of her fingertips, bearing fingernails, into the finger-cups 700 and the machine is activated to perform EPR on all three (or in an alternative embodiment, four) fingernails simultaneously. In an alternative embodiment, an optional plate 758 is present to create a gradient in the magnetic field between poles 750 to permit separate measurement of the three fingernails; the separate measurements may be combined into a total dose for the subject or may be reported separately. Once measurements are determined, a radiological triage tag or triage tag sticker may be printed on printer 760 and a patient record in a database on a recordkeeping database computer 762 may be updated with the measurements and triage category determined by the measurement and computing device 754.

Whole-body radiation dose measurements may also be made by measurements of EPR resonances in the enamel of human teeth, such as molars.

Prior techniques of measuring EPR resonances in human teeth have required either tooth removal, or use of a semirigid waveguide for coupling the apparatus for measuring radio frequency resonances to the teeth in vivo. It is not practical to remove teeth for screening large numbers of potential victims during or after a mass disaster—as such removal is likely permanent and tooth removal will likely be resisted by the potential victims. While the use of a semirigid waveguide as known in the art is feasible, the use of the EPR spectrometry in the field, as necessary for triage applications, is greatly simplified by use of a flexible connector or transmission line attached to a flexible pickup coil. Resolution of lower doses of radiation is made easier by combining information derived from measurements from more than one tooth and/or more than one fingernail.

Figure 20:
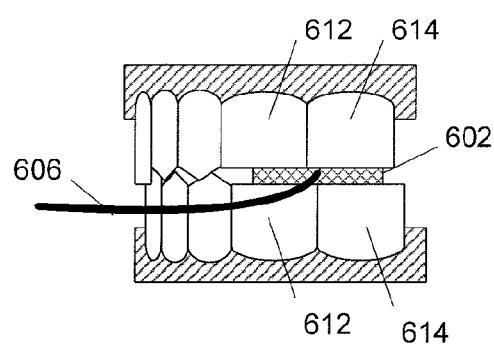
FIG. 20 is a side view of a sensing loop device clenched between teeth of a subject.
Figure 23:
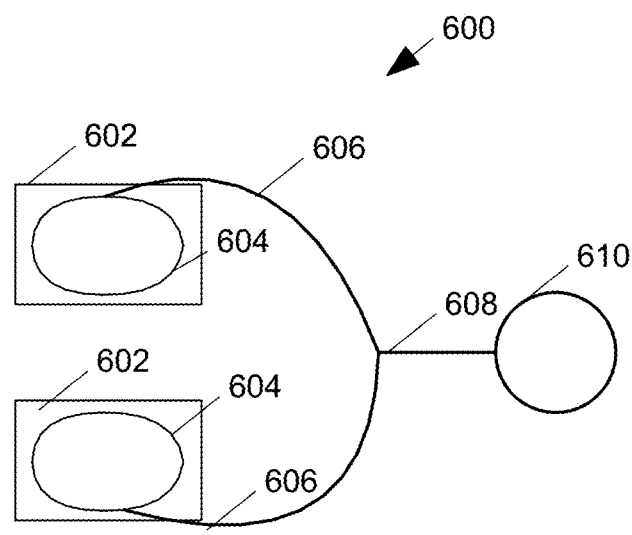
FIG. 23 is an illustration of a sensing loop device for use between teeth of a subject.

The embodiment of FIGS. 20 and 23 utilizes a resonator comprising a thin plastic chip 602 of thickness between one and two millimeters, of width six millimeters, and of length about one centimeter. This replaceable resonator greatly resembles the resonator previously described with reference to FIG. 21, but the plastic chips 602 and sensing coils 604 are somewhat larger and sturdier than those used with fingernails. Each such plastic chip 602 has embedded within it a sensing coil 604 of one to two turns of enameled copper wire and average diameter of seven millimeters. Each of the two sensing coils 604 is coupled through a twisted transmission section 606 to a common transmission section 608 and to a pickup coil 610 of about one centimeter diameter. The pickup coil 610 may either be a continuous loop, or may have a capacitive pigtail tuning element. The capacitive pigtail tuning element represents a point where the pickup coil loop is discontinuous; with its two ends twisted tightly together for a distance that provides suitable coupling capacitance between the ends.

In use, the plastic chips are clenched between a subject's upper and lower first molars 612 and second molars 614, thereby providing coupling to enamel of these teeth, four on each side and eight total, for EPR sensing. Other teeth also may be used, depending on the dental health of the subject, but this requires use of separate calibration data tables. The pickup coil is magnetically coupled by appropriate wire to apparatus for measuring a radiofrequency resonance as with the embodiment of FIG. 17. The assembly of chips, transmission sections, and pickup coil is essentially as for the device of FIG. 21, although larger diameter wire may be used; a wire loop is formed, transmission sections are pinched together and twisted, and remaining sections form sensing and pickup loops. The sensing coils, and optionally the coupling coil, are then cast into the plastic chips, and the entire assembly coated with insulating plastic. The simple construction of the plastic chips and associated transmission sections and pickup coils allows for low cost and easy replacement, as these components are likely to suffer eventual damage when chewed by large numbers of people. In an embodiment, the chips are made for one time use, eliminating need for sterilization of chips or replacement of chip covers between uses.

In use, the device of FIG. 23 is placed into the subject's mouth and clenched between teeth. The subject's head is then inserted between poles of a magnet wide enough to allow placement of the head between pole pieces, and EPR spectra are measured. In an embodiment, the magnet is preferably about 400 gauss and the resonance occurs at about twelve hundred megahertz when measuring EPR of teeth and using a coupler having pickup coils 604 of from one to two turns of copper wire embedded in the plastic chips 602, coupled by twisted-pair transmission line portions 606 to a coupling coil 610. Since teeth are relatively dry and absorption of radio frequency energy by water is not as significant an issue as with intact, uncut, fingernails, this embodiment also is expected to operate at 2.4 GHz with an appropriate magnetic field, and may also operate at some higher frequencies—possibly even at 9.5 GHz. In those subjects where radiation exposure is detected, a nonuniform magnetic field may be used to separately determine resonances from left and right teeth to detect asymmetrical exposure or invalid data due to improper chip placement, tooth loss or decay, or dental work on one or more teeth. Where valid data is obtained from both left and right teeth this data may be averaged to provide a more accurate measure of subject radiation exposure.

This use is illustrated with the use of molar teeth, but it also can be used with any teeth, so that in subjects with missing molars or extensively restored molars, the measurements may still be made using premolars, canines, and incisors, although different calibration tables may need to be used because of the reduced mass of enamel near the coils 604. For example, in subjects lacking molars, the plastic chips of the device of FIGS. 23 and 20 may be held between lip and upper incisors to obtain dosimetry information from the enamel of the incisors.

The device of FIG. 23 provides a measure of total radiation exposure of the subject since the teeth formed, which may often include some radiation exposure incurred by the subject many years before the measurement is made. The cumulative radiation dose includes radiation received from most causes such as the normal environment at 3 to 4 mSv per year and diagnostic X-rays at from 0.1 mSv for a chest X-ray to 10 mSv for a CT-scan, is typically well below the one Sievert or higher level that requires triaging into the medical system for treatment of acute radiation sickness. Therapeutic radiation to the oral cavity or neck may also have resulted in a prior exposure to teeth that would appear to be in the range of requiring acute medical treatment if received as a whole body exposure, this eventuality could be uncovered with appropriate medical history taking and by estimation of dose with EPR of fingernails in those subjects.

There is little biological difference between fingernails and toenails. Both have high keratin content and will develop both mechanically induced signals when clipped, although growth rate and average thickness may differ. Both will develop radiation induced EPR signals when exposed to ionizing radiation. They have some differences in detail, such as moisture content and thickness, because toenails generally grow at a slower rate. The machines described herein with respect to fingernail dosimetry are applicable to toenail dosimetry as well, although it may prove necessary to use separate stored calibration information for toenails and fingernails in measurement and computing apparatus 754 for eliminating the MIS signal, determining the RIS portion of the signal, and translating RIS into exposure. In an embodiment resembling that of FIG. 8, the bar code that may be applied to the sample holder 202 includes an indicator of whether the sample is a toenail clipping or a fingernail clipping; the machine then selects the appropriate calibration information for computing radiation dose from RIS from a set of fingernail calibration information and a set of toenail calibration information stored in memory of electronics 212, 246, 312, 706, 760.

Measurement of radiation exposure using EPR fingernails of both hands and toenails of both feet may also prove useful to guide treatment in those subjects who have received radiation doses substantial enough to require treatment because differences in RIS between limbs can indicate when subjects have received uneven exposure. This is important because those subjects who have received uneven exposure may have more viable bone marrow or stem cells in those limbs that have received lower exposure than in those body parts that received higher exposure, and the viable bone marrow or stem cells may seed those body parts that received higher exposure.

Figure 22:
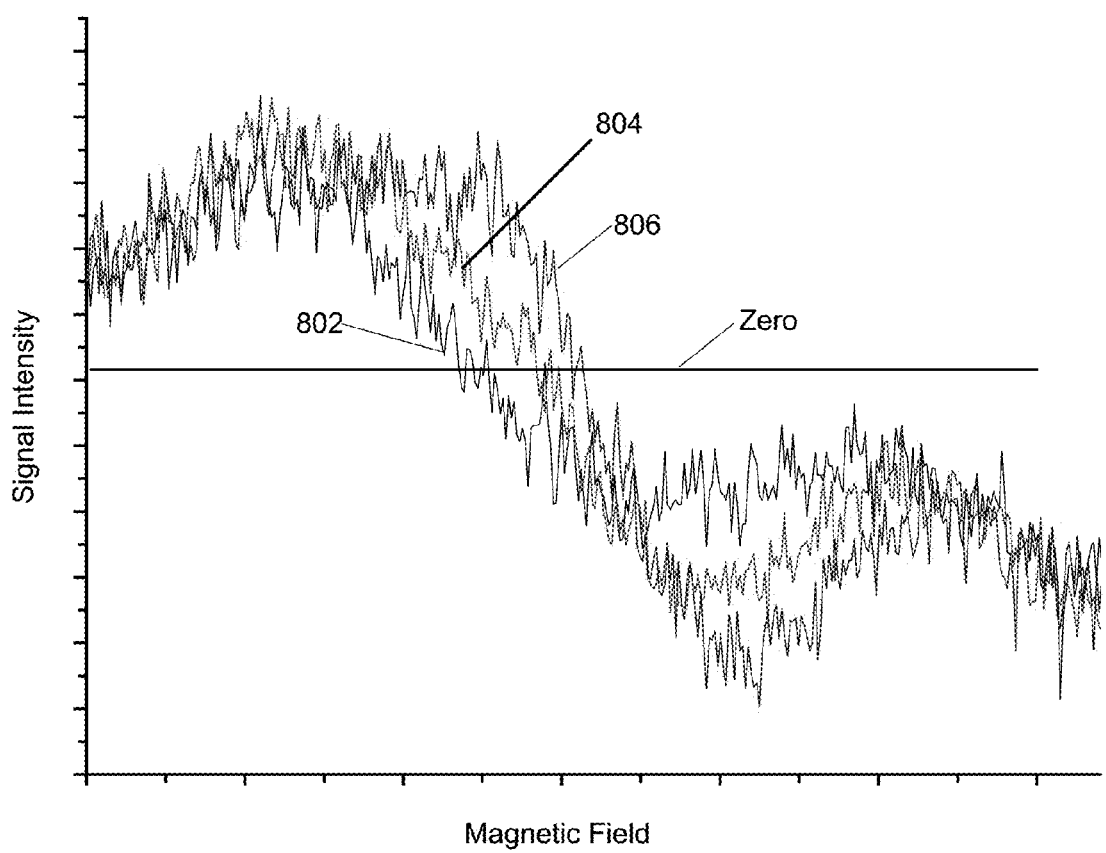
FIG. 22 is an illustration of the shift in frequency of zero-crossover of the resonances with increasing radiation dose.

With reference to FIG. 22, it has also been observed that, in a field or frequency window of a few tenths of a percent near the crossover point 795 (FIG. 15) of the composite of mechanically and radiation induced signals, the crossover point shifts slightly in the direction of higher field or lower frequency when a strong radiation-induced signal is present, see FIG. 22. FIG. 22 portrays the zero-crossover region spectra of a fingernail sample that has not been irradiated 802, the crossover region spectra of one that has been irradiated at five grays 804, and one that has been irradiated at ten grays 806. All three spectra were taken two minutes after the irradiated or un-irradiated samples were cut into five pieces and placed into a sample holder.

In an alternative embodiment intended for triage purposes in exposed subjects, the RIS is estimated, and triage categories determined, based on the amount of shift in this crossover point and the amount of time and storage temperature since a sample was cut because this shift has been observed to drift with time after cutting. This embodiment determines the shift by using an EPR standard present in the same magnetic field and present in the same spectra as a reference, and determining a difference in frequency or field of the crossover point of the fingernail signal relative to a crossover point of the signal due to the reference.

Figure 24:
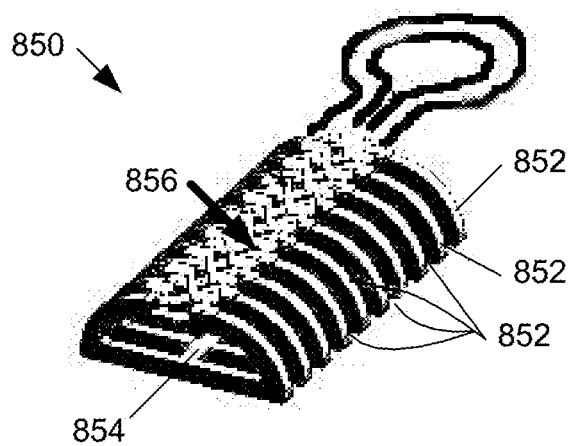
FIG. 24 is a view of an alternative embodiment of a sensing loop device for use in sensing EPR measurements of fingernails as illustrated with reference to FIGS. 17, 18, and 19.

It has been found that resonances in fingernails are more readily detectable and provide a clearer RIS when taken at higher magnetic field strengths and correspondingly higher frequencies. As frequencies are increased, however, non-resonant absorption of radio frequency energy by water in tissues adjacent to intact fingernails becomes an increasingly significant issue. An alternative embodiment for use in measuring radiation dose absorbed by intact fingernails in vivo employs high frequencies, of between 9 and 10 GHz and about 9.5 GHz, with a magnetic field of around 3300 gauss to take advantage of this increased sensitivity. In order to limit penetration of the radio frequency energy into tissues, such as the nailbed, adjacent to or near the fingernail, and attenuation associated with such penetration, this embodiment uses a surface-sensitive resonator 850 (FIG. 24). Other portions of this embodiment resemble those illustrated in FIGS. 17, 18, and 19.

Figure 27:
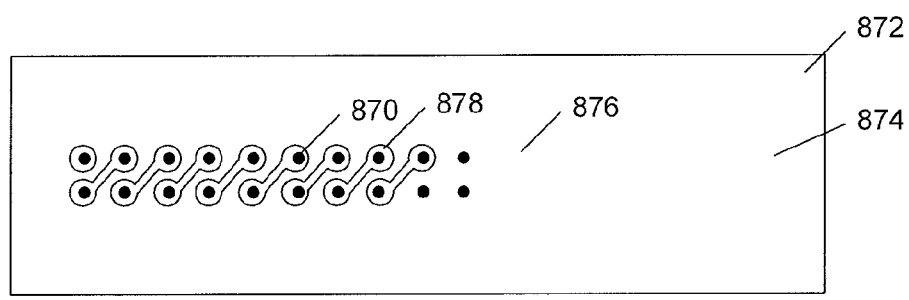
FIG. 27 is a top view of the printed circuit board of the device of FIG. 24.

The resonator 850 for use near 9.5 GHz has several closely-spaced D-shaped elements 852 joined by a backbone 854 located in the center of the straight arm or back of the D. Circuitry 856 is provided on a circuit board (not shown in FIG. 24 for clarity, see FIGS. 27 and 28) to reverse polarity in, thereby reversing currents in, adjacent D-shaped elements 852, to produce counter-rotating-currents (CRC) in the D-shaped elements. The CRC causes the electromagnetic fields associated with adjacent D-shaped elements to cancel at distances significantly greater than a spacing of the D-shaped elements 852, while being significant close to the elements.

Because the electromagnetic fields associated with the CRC resonator of FIG. 24 cancel at depths more than a couple of millimeters from the resonator, these fields are most intense and are sensitive to resonances in the fingernail without substantial attenuation by underlying tissues of the finger.

Figure 25:
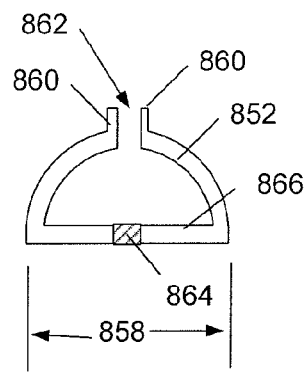
FIG. 25 is a view of one D-shaped element of the sensing loop device of FIG. 24.

An individual D-shaped element 852 is illustrated in FIG. 25. It has a pin 860 on each side of a gap 862 in the curved arm of the D. The backbone 864 in the straight arm 866 of the D is sectioned in the illustration.

In an alternative embodiment resembling that of FIG. 24, the back of each D 852 is slightly concave to more closely fit normal fingernail curvature.

Figure 26:
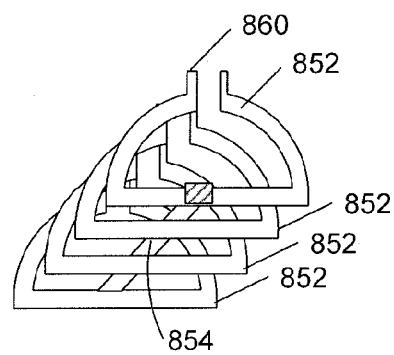
FIG. 26 is a view of several D-shaped elements and their backbone of the device of FIG. 24.

The D-shaped elements 852 are formed by electric discharge machining as a group of from six to ten elements with backbone 854 connecting them as shown in FIG. 26. In an embodiment, the elements 852 are spaced along the backbone with pitch about one millimeter of width 858 of the D about five millimeters The pins 860 of the D-shaped elements 852 are inserted and soldered into plated-through holes 870 (FIG. 27) in a printed-circuit board 872. Circuit board 872, which may be a thin and flexible circuit board, has an etched foil coupling loop 874 that may inductively couple to the pickup coil 668 of electronics 674 in the machine illustrated in FIG. 17. The circuit board has a transmission line portion 876 for transmitting radio frequency energy to the D-shaped elements 852, and which in an alternative embodiment is bent at a 90-degree angle to avoid stray coupling of a 9.5 GHz signal into radiation-absorbent tissues from pickup coil 668 and coupling loop 875. The circuit board also has a pattern of connecting pads and lines 878 that alternate polarity of driving signals at each D-shaped element 852.

Figure 28:
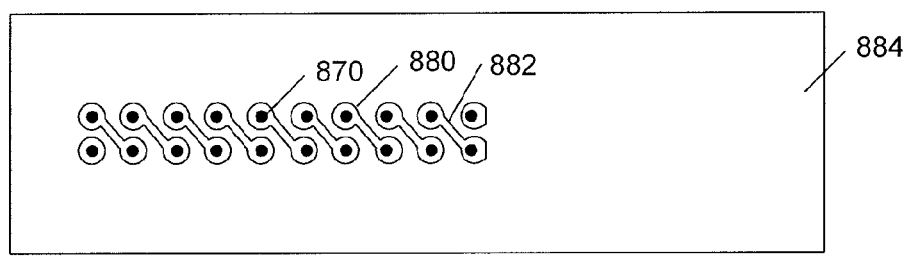
FIG. 28 is a top view of a bottom layer of the printed circuit board of the device of FIG. 24.

In order to complete the alternating polarity of driving signals at each D-shaped element 852, a second or bottom layer 884 of the printed circuit board—shown as a top view so its relationship to the top layer of Figure of 27—is provided as illustrated in FIG. 28. This has the plated through holes 870 also illustrated in FIG. 27, with a pattern of pads 880 and lines 882 that complete the circuit to reverse polarity of driving signals between each D-shaped element 852, thereby providing alternating current direction between each pair of elements 852.

The embodiment of FIG. 17 using the resonator of FIGS. 24-28 is particularly well adapted to triage and diagnostic applications because the resonator can be positioned to avoid the fingernail ends and thereby avoid the mechanically induced signals MIS heretofore discussed; the remaining signal is primarily RIS.

An embodiment of the resonator of FIGS. 24-28 is surface sensitive, in that it is sensitive primarily to material within the range of in contact with the resonator to two millimeters of the resonator. By being sensitive primarily to material within a certain range of distances we mean that, when in contact with a fingernail or other substance exhibiting EPR resonance, eighty percent or better of the resonance signal measured is derived from interactions with substances located within this range of distance from a base of the resonator. An alternative embodiment is primarily sensitive to materials within one and a half millimeters of the resonator.

While the forgoing has been particularly shown and described with reference to particular embodiments thereof, it will be understood by those skilled in the art that various other changes in the form and details may be made without departing from the spirit and scope hereof. It is to be understood that various changes may be made in adapting the description to different embodiments without departing from the broader concepts disclosed herein and comprehended by the claims that follow.

What is claimed is:

1. Apparatus for performing electron paramagnetic resonance (EPR) spectrometry in fingernails in vivo comprising:
    a magnet;
    a device for positioning at least one resonator, upon a dorsal surface of a finger adjacent to at least one fingernail, the resonator having a twisted-pair transmission-line section between a coupling coil and a pickup coil;
    a radio frequency measuring device coupled to the coupling coil of the at least one resonator for determining an EPR spectra;
    a processing system for computing a radiation dose based upon the EPR spectra, and for comparing the radiation dose to triage limits to determine a triage classification; and
    apparatus for outputting the triage classification.

2. The apparatus of claim 1 wherein the device for positioning positions a plurality of resonators, upon dorsal surfaces of a plurality of fingers adjacent to a plurality of fingernails.

3. The apparatus of claim 2 wherein the device for positioning comprises a plurality of finger-cups made of an elastomeric material.

4. The apparatus of claim 1 wherein the magnet provides a magnetic field having strength of at least two thousand gauss, and wherein the magnet comprises a permanent magnet.

5. The apparatus of claim 4 wherein a reference sample comprising manganese or molybdenum is present within the magnetic field.

6. The apparatus of claim 1 wherein the apparatus for outputting the triage classification comprises a printer for printing an output selected from the group consisting of a radiological triage tag and a radiological triage sticker.

7. The apparatus of claim 2 wherein the apparatus measures EPR spectra of at least two fingernails simultaneously.

8. The apparatus of claim 2 wherein the resonators are primarily sensitive to material within two millimeters of the resonator.

9. The apparatus of claim 8 wherein the at least one resonator is a counter-rotating-current resonator.

10. Apparatus for performing electron paramagnetic resonance (EPR) of at least one nail clipping, the nail clipping from a fingernail or a toenail of a subject, comprising:
    at least one EPR measurement station comprising;
    a magnet for providing a magnetic field and a coupling coil;
    an RF generation and measurement system coupled to the coupling coil; and
    a processor coupled to the RF generation and measurement system for obtaining EPR spectra of the at least one nail clipping;
    wherein the processor obtains first EPR spectra at at least a first and a second power level to estimate a component of a mechanically induced signal in the EPR spectra;
    wherein the processor determines a radiation-induced signal by a method comprising subtracting the component of the mechanically-induced signal from at least one of the EPR spectra; and
    wherein the processor determines a radiation dose from the radiation induced signal; the apparatus further comprising
    a magazine for containing a plurality of clipping-holders, each clipping holder for holding at least one nail clipping; and
    apparatus for feeding clipping holders from the magazine into the at least one EPR measurement station;
    wherein the magazine is held at a temperature below zero Celsius.

11. The apparatus of claim 10 further comprising a holding bay maintained at a temperature of at least twenty degrees Celsius, wherein the processor obtains an additional EPR spectra after the nail clipping is held for a time in the holding bay, wherein the additional EPR spectra is used by the processor together with the first EPR spectra to determine a second component of the mechanically induced signal, and wherein the method for determining the radiation induced signal further comprises subtracting the second component of the mechanically induced signal from an EPR spectra.

12. The apparatus of claim 11 wherein the processor obtains the additional EPR spectra using an additional EPR measurement station.

13. The apparatus of claim 10 wherein the radiation dose is compared to triage limits to determine a triage category for the subject, and wherein the apparatus further comprises a printer for printing the triage category.

14. The apparatus of claim 13 wherein the printer prints a triage report for the subject, the triage report comprising a report selected from the group consisting of a triage tag, a sticker for application to a triage tag, and a printed report.

15. The apparatus of claim 13 wherein the printer prints the triage category on the clipping holder.

16. The apparatus of claim 11 further comprising a radiation source, wherein the fingernail clipping is exposed to the radiation source after the additional EPR spectra is obtained, and wherein a fourth EPR spectra is obtained by the processor after the fingernail clipping is exposed to the radiation source.

17. Apparatus for performing electron paramagnetic resonance (EPR) spectrometry in teeth in vivo comprising:
 a magnet having sufficient space between poles for a subject's head to be positioned between the poles;
 at least one resonator having an encapsulated pickup coil for placement between or adjacent to at least one tooth of the subject, the resonator having a twisted-pair transmission-line section between a coupling coil and the pickup coil;
 a radio frequency measuring device coupled to the at least one resonator for determining at least one EPR spectrum;
 a processing system for computing a radiation dose based upon the EPR spectrum, and for comparing the radiation dose to triage limits to determine a triage classification; and
 apparatus for outputting the radiation dose and the triage classification.

18. The apparatus of claim 17, the resonator further comprising a second encapsulated pickup coil for placement between or adjacent to at least one additional tooth of the subject.

19. The apparatus of claim 17 wherein a reference sample comprising manganese or molybdenum is present within the magnetic field.

20. The apparatus of claim 17 wherein the apparatus for outputting the triage classification comprises a printer for printing an output selected from the group consisting of a radiological triage tag and a radiological triage sticker.

21. The apparatus of claim 17 wherein the apparatus measures EPR spectra of at least two teeth simultaneously.

* * * * *